United States Patent [19]

Smith et al.

[11] Patent Number: 5,037,760

[45] Date of Patent: Aug. 6, 1991

[54] SECRETORY SIGNAL SELECTION VECTORS FOR EXTRACELLULAR PROTEIN SYNTHESIS BACILLI

[75] Inventors: Hilde E. Smith, Groningen; Jan H. Van Ee, Nieuwerkerk a/d IJssel; Ben P. H. Peeters, Haren; Sierd Bron, Haren; Gerard Venema, Haren, all of Netherlands

[73] Assignee: Gist-brocades NV, Delft, Netherlands

[21] Appl. No.: 45,890

[22] Filed: May 1, 1987

[30] Foreign Application Priority Data

May 2, 1986 [EP] European Pat. Off. ........ 86200774.7

[51] Int. Cl.$^5$ .................. C12N 15/00; C12N 1/20; C12P 21/06; C12P 19/34
[52] U.S. Cl. .................. 435/320.1; 435/69.1; 435/69.8; 435/91; 435/172.1; 435/252.31; 435/252.35; 435/252.5
[58] Field of Search .................. 435/68, 70, 91, 172.1, 435/172.3, 320, 832, 283, 839, 849, 69.1, 69.8; 530/300; 536/27; 935/6, 9, 38, 39, 47, 48, 56

[56] References Cited

U.S. PATENT DOCUMENTS

| | | | |
|---|---|---|---|
| 4,585,739 | 4/1986 | Lovett et al. | 435/253 |
| 4,663,280 | 5/1987 | Sloma | 435/68 |
| 4,711,843 | 12/1987 | Chang | 435/68 |
| 4,769,327 | 9/1988 | Stephens et al. | 435/68 |

OTHER PUBLICATIONS

Pouwels et al., Cloning Vectors, A Laboratory Manual, Elsevier Publ. (1985).
Maniatis, T. et al. Molecular Cloning, A Laboratory Manual, Cold Spring Harbor Laboratory, CSH, NY (1982).
Ohmura, K. et al. J. Biochem. vol. 95, pp. 87–93 (1984).
Vieira, J. et al. Gene, vol. 19, pp. 259–268 (1982).
Yang, M. et al. Nucl. Acids Res. vol. 11, pp. 237–249 (1983).
Kazutaka, et al., Chemical Abstracts, vol. 100 Abstract No. 80657r (1984).
Watson, Nucl. Acids Res. vol. 12, pp. 5145–5163 (1984).

*Primary Examiner*—Richard A. Schwartz
*Assistant Examiner*—Joan Ellis
*Attorney, Agent, or Firm*—Barabara Rae-Venter; Bertram I. Rowland

[57] ABSTRACT

Novel vectors are provided for identifying secretory signal sequences from DNA fragments of unicellular microorganisms. The plasmids comprise a multiple cloning site with restriction sites in reading frame with a structural gene which permits rapid screening of the screted expression product. Optionally, the vectors may include a promoter region upstream from the multiple cloning site. The invention is exemplified with Bacillus. Specific secretory signal sequence have been isolated with those vectors, allowing for efficient secretion into the supernatant, and not just to the periplasmic space to provide proteins in economically high yields. Secretory sequences are provided superior to other previously known sequences.

6 Claims, 7 Drawing Sheets

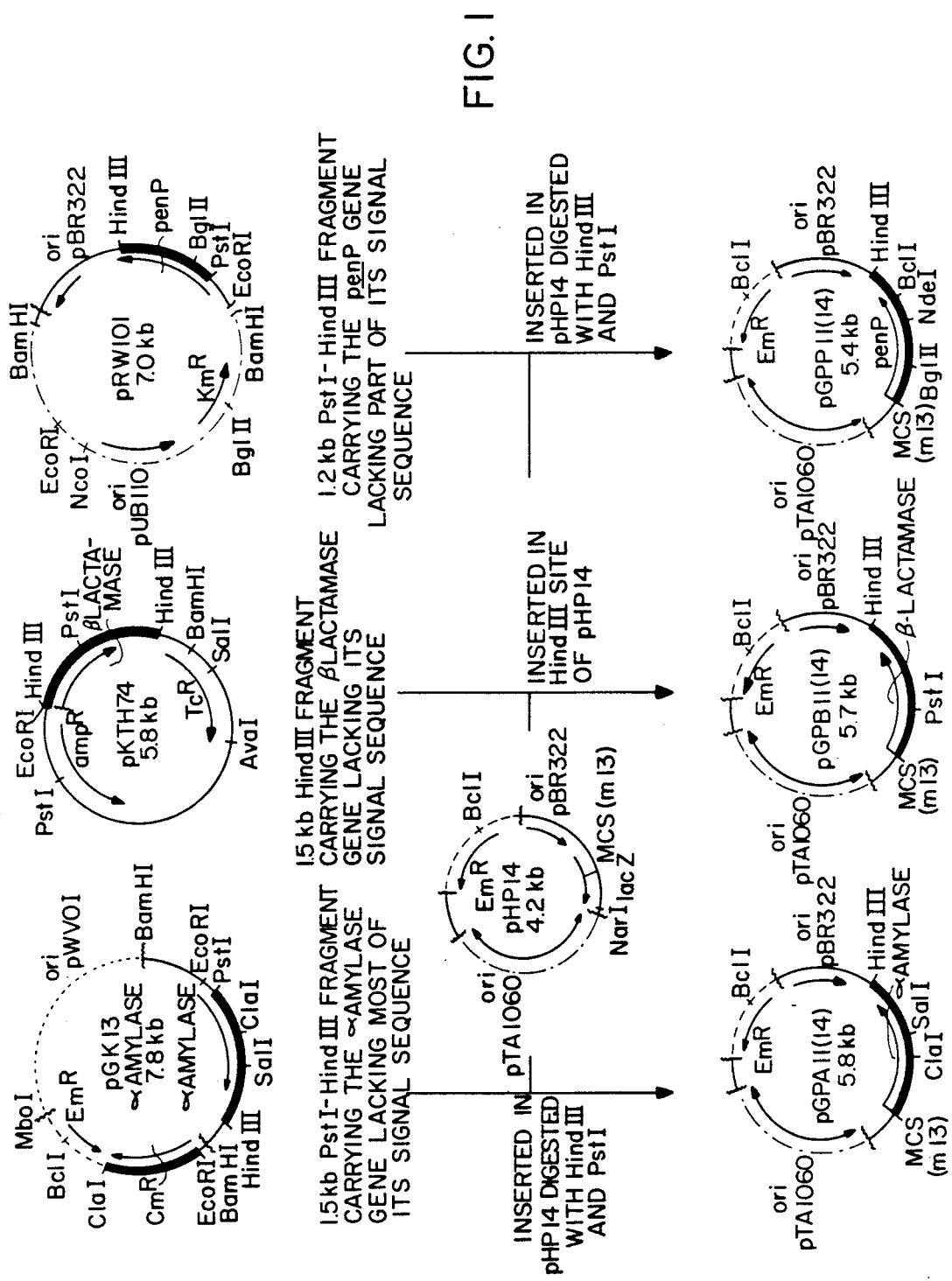
FIG. I

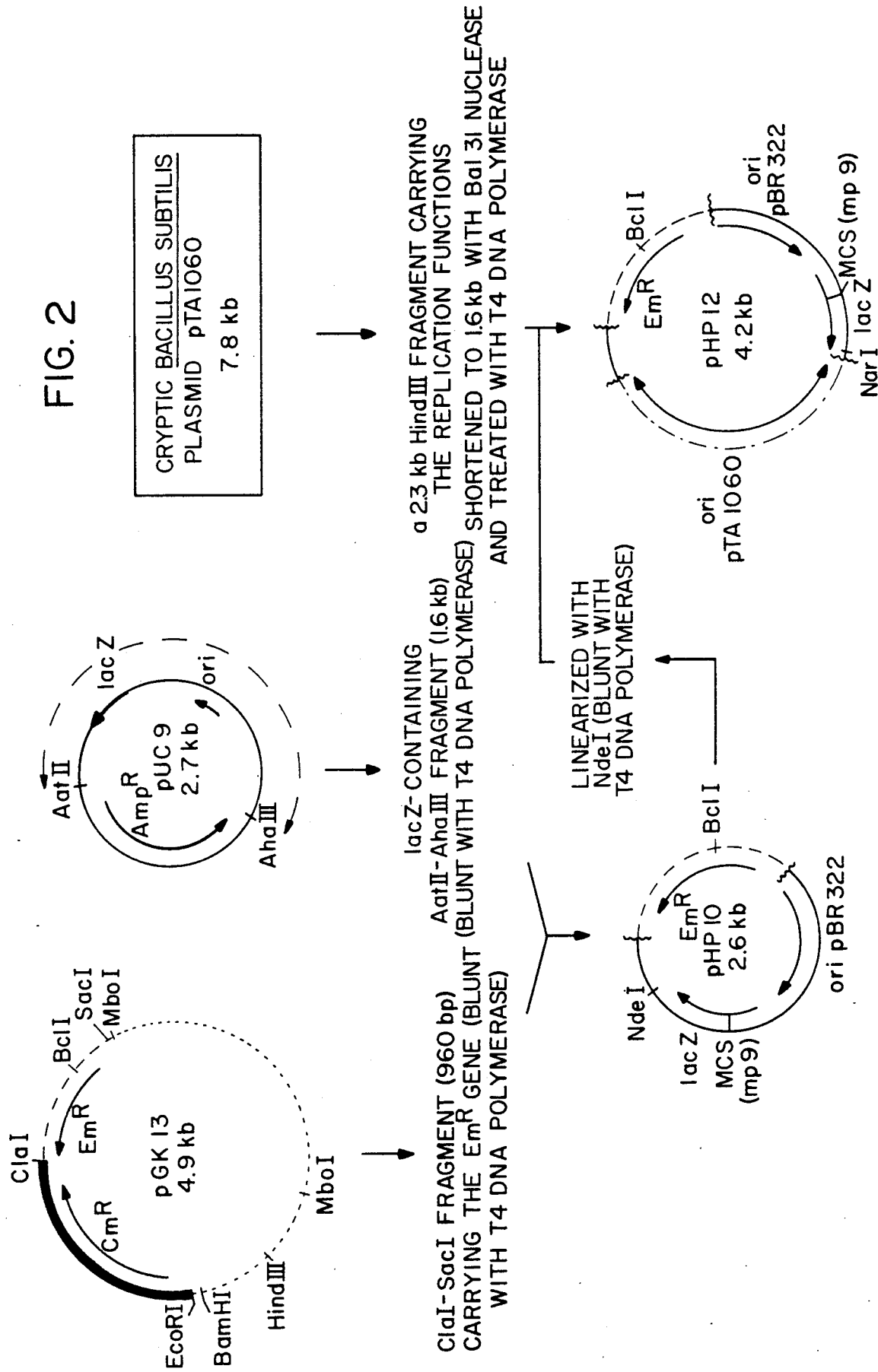

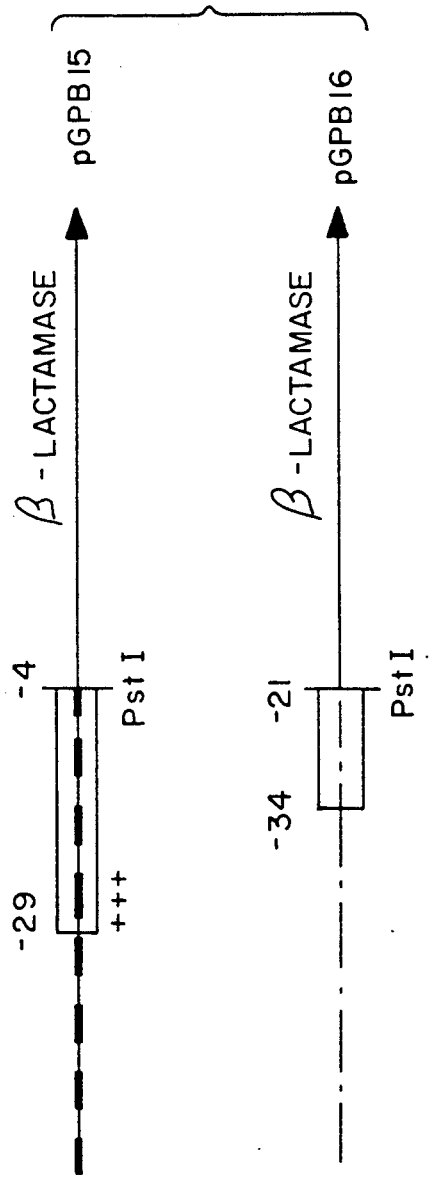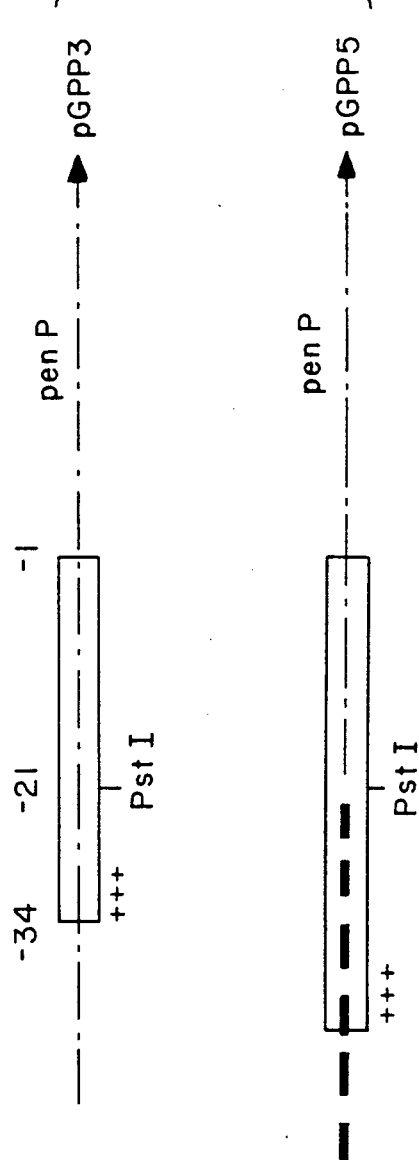

SECRETORY SIGNAL SELECTION VECTORS FOR EXTRACELLULAR PROTEIN SYNTHESIS BACILLI

FIELD OF THE INVENTION

This invention relates to secretory signal selection vectors and the use of the secretory signal sequence identified with these vectors for high yield production of extracellular proteins, preferably enzymes, in recombinant DNA-containing microorganisms of the genus Bacillus.

BACKGROUND OF THE INVENTION

Bacilli have a very long history of use in industrial large scale fermentation because of some very advantageous properties. They are capable of growing on rather cheap nutrients, they do not produce endotoxins so that they are harmless for man, plants and animals, and they are capable of synthesizing many industrially interesting proteins, such as enzymes, as extracellular products which in most cases can be isolated rather easily. This combination of characteristics, in particular the secretion of products into the culture medium, makes the use of Bacilli for commercial purposes much more attractive than for example the use of *E. coli*. In order to improve the economic value of Bacilli even further, many attempts have been made to develop a Bacillus host-vector system, both for homologous and heterologous gene expression. See, for example, D. Dubnau in "Experimental Manipulation of Gene Expression" Academic Press (1983) 33–51 and R. H. Doi, *Biotechnology and Genetic Engineering* (1984) 2:126–155.

Unfortunately, however, the level of expression and secretion appeared to be relatively low. See, for example, S. Kovacevic et al., *J. Bacteriol.* (1985) 162:521–528, C. W. Saunders et al., *J. Bacteriol.* (1984) 157:718–726, R. Ohmura et al., *J. Biochem.* (1984) 95:87–93, Book of Abstracts of the 3rd International Conference on Genetics and Biotechnology of Bacilli, Stanford USA (1984), K. Lundström, *FEMS Letters* (1984) 23:65–70, I. Palva et al., *Gene* (1983) 22:229–235, K. Lundström et al., *Virus Res.* (1985) 2:69–83, K. Hardy et al., *Nature* (1981) 293:481–483, K. Mosbach et al., *Nature* (1983) 302:543–545, S. Chang et al., *NSC Ser. Gene* (1981) 16:199–206 and J. I. Flock et al., *Mol. Gen. Genet.* (1984) 195:246–251.

Many improvements of the Bacillus cloning system have already been reported with respect to increased expression to an economically acceptable level. They are mainly related to improvements of the promoter region in order to increase the transcription efficiency (D. M. Williams et al., *J. Bacteriol.* (1981) 146:1162–1165, R. G. Schoner et al., *Gene* (1983) 22:47–57, D. S. Goldfarb et al., *Nature* (1981) 293:309–311, L. Band et al., *Gene* (1983) 26:313–315, C. E. Donelly and A. L. Sonnenshein, *J. Bacteriol.* (1984) 157:965–967 and Dutch patent application No. 86/201951.0), but they also concern improvements on the Shine-Dalgarno region in order to increase the translation efficiency (A. Hui et al., *EMBO Journal* (1984) 3:623–629, H. de Boer et al., *DNA* (1983) 2:231–235, L. Band and J. Henner, *Biochem. Soc. Symp.* (1984) 48:233–245 and European patent application no. 86/201951.0). The construction and use of vectors that permit isolation, improvements and use of secretory signal sequences, however, have not been reported so far.

Most of the current understanding of protein secretion in prokaryotic cells is limited to *E. coli*, (L. L. Randall and S. T. S. Hardy, *Mirobiol. Reviews* (1984) 48:290–298 and S. A. Benson et al., *Ann. Rev. Biochem.* (1985) 54:101–134). In *E. coli*, a gram-negative organism, the secretion of a protein is in fact the transport to the periplasm rather than to the culture medium as is the case in Bacillus, a gram-positive organism. The knowledge of protein secretion in *E. coli* has mainly been obtained by the study of fusion proteins containing a segment of a protein which is known to be translocated to the periplasm, attached to β-galactosidase.

A very serious limitation in the use of such hybrid proteins is that the β-galactosidase moiety appears to be unable to pass through the *E. coli* cytoplasmic membrane, cf. C. S. Hoffman and A. Wright, *Proc. Natl. Acad. Sci. USA* (1985) 82:5107–5111. Although this problem has been overcome by the use of alkaline phosphatase instead of β-galactosidase (C. Monoil and J. Beckwith, *Proc. Natl. Acad. Sci. USA* (1985) 82:8129–8133), the authors describe their results, obtained with some hybrid alkaline phosphatases as transport from the cytoplasm into the periplasm rather than as secretion into the culture medium.

SUMMARY OF THE INVENTION

This invention provides for secretory signal sequence selection vectors which allow for isolation of signal sequences providing secretion of proteins in economically high yields. It was surprisingly found that certain signal sequences are much more efficient than other sequences regulating high secretion levels of known extracellular Bacillus proteins. Therefore, this invention provides for an improvement in extracellular protein yields, both of proteins, homologous or heterologous, which were not secreted efficiently so far and of proteins (for example, enzymes) that are already secreted efficiently.

DESCRIPTION OF THE FIGURES

FIG. 1—Construction of plasmids pGPA11, pGPB11 and pGPP11

This figure shows the cloning strategy for the construction of pGPA11, pGPB11 and pGPP11. The origins of plasmid segments are indicated in the key. Only those restriction sites relevant for the construction and properties of the recombinant plasmids are shown.

FIG. 2—Construction of plasmid pHP12

This figure shows the cloning strategy for the construction of pHP12. The origins of plasmid segments are indicated in the key. Only those sites relevant for the construction and properties of the recombinant plasmid are shown. Plasmid pHP14 was constructed similarly, except that the 1.6 kb AatII-AhaIII fragment was taken from pUC13.

Figure 3A:
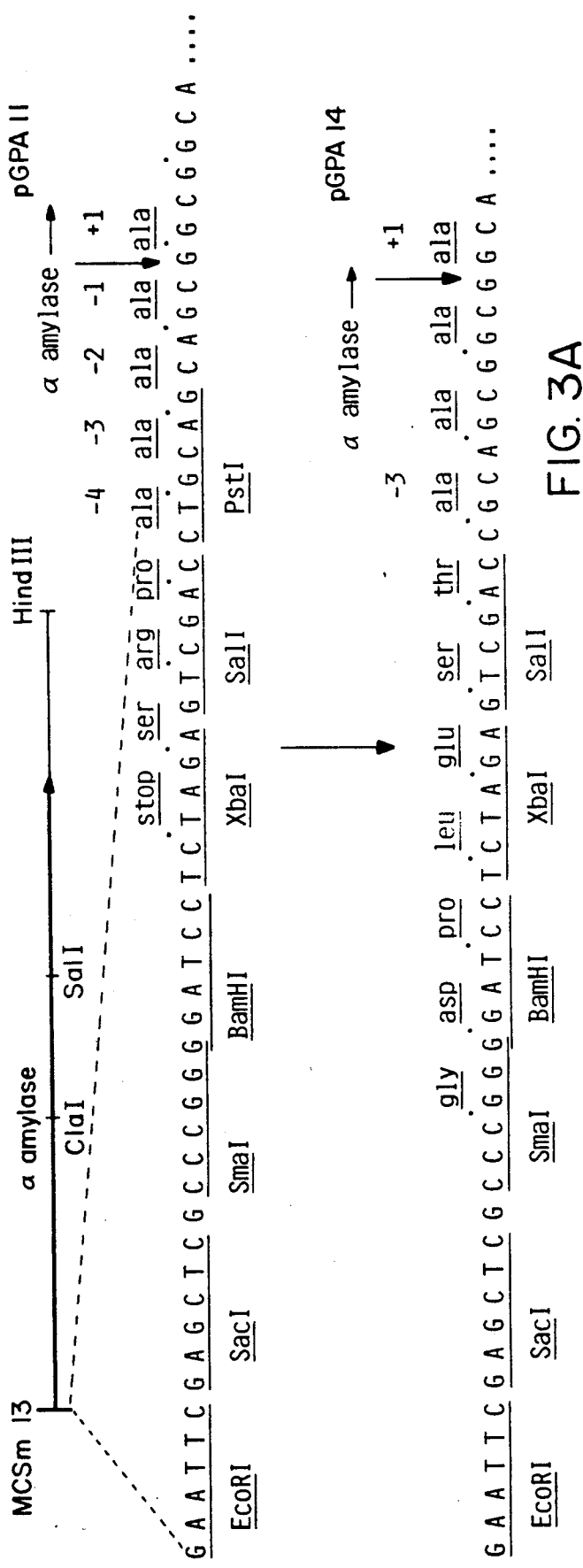
Figure 3B:
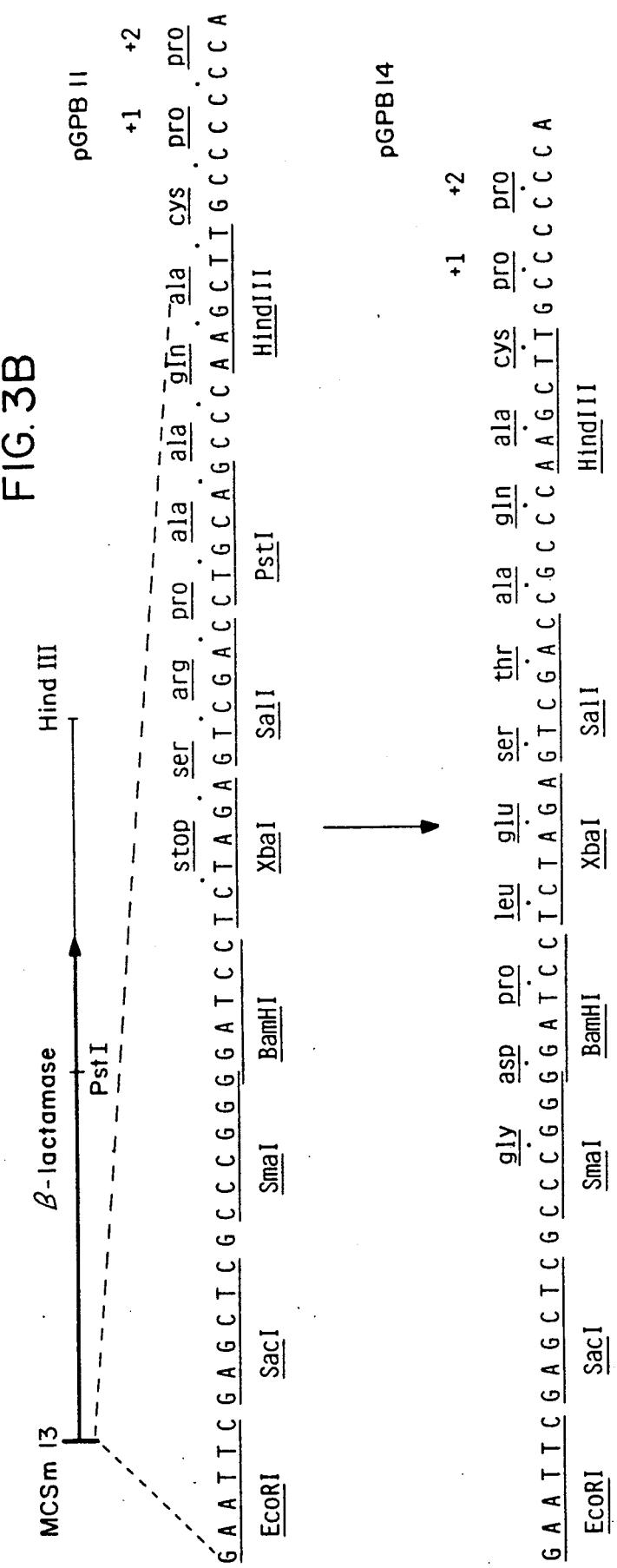

FIG. 3—Construction of plasmids pGPA14, pGPB14 and pGPP14

Figure 3C:
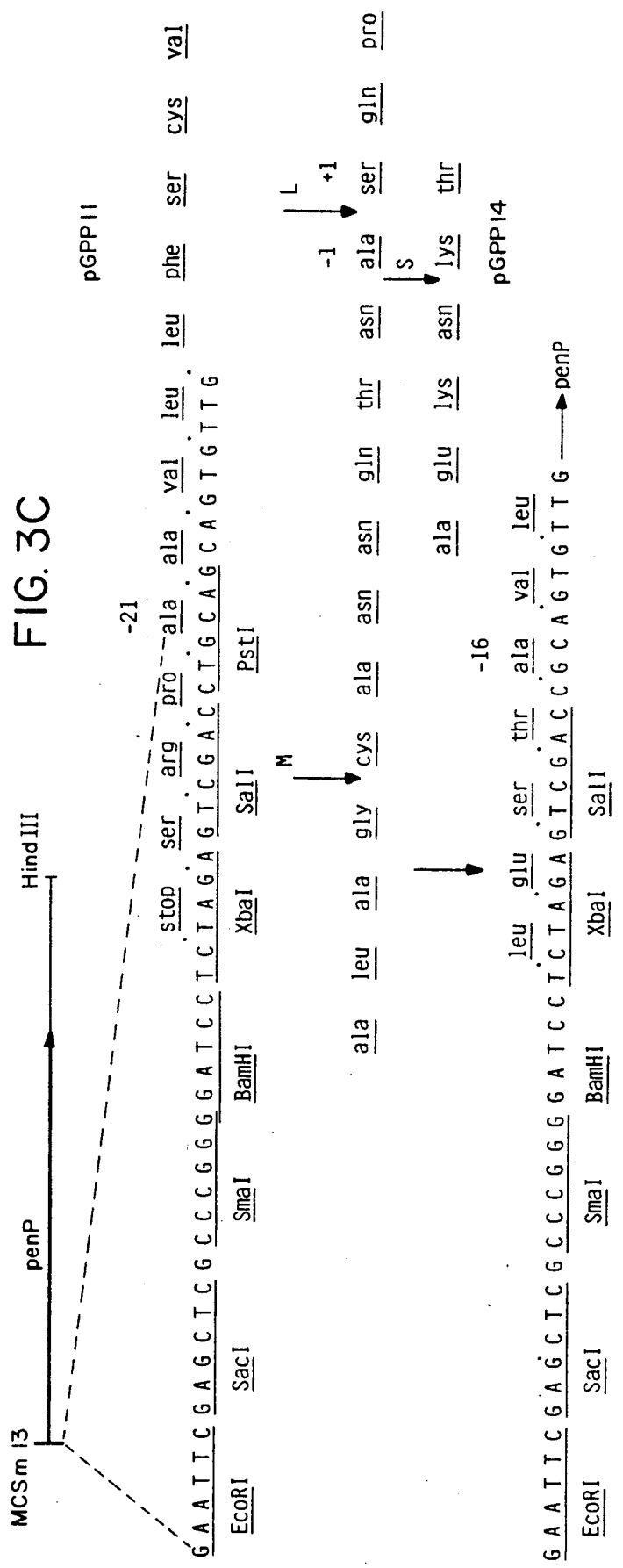

This figure shows the DNA sequences at the fusion points of the multiple cloning sites (MCS) with the structural genes (A: α-amylase; B: β-lactamase; C: penP). The vertical arrows in FIGS. 3A and 3C indicate the original cleavage sites for leader peptidase. Several codons around the processing sites are numbered and the corresponding amino acids are indicated in italics. The plasmids pGPA14, pGPB14 and pGPP14 derivatives were constructed by digesting pGPA11, pGPB11 and pGPP11, respectively, with PstI followed by chewing back for blunt ending with T4 DNA polymerase. In FIG. 3C, L indicates the processing site to the large extracellular form of penicillinase; M indicates the membrane-bound form of penicillinase. The plasmids pGPA14, pGPB14 and pGPP14 were deposited in *Bacillus subtillus* strain 8G-5 on May 2, 1986 under the provisions of the Budapest Treaty with the Centraal Bureau of Schimmelcultures, Oosterstraat 1, NL-3742 SK Baarn, and were allotted numbers CBS 245.86, CBS 246.86 and CBS 247.86, respectively.

FIG. 4—Construction of plasmids pGPB15 and pGPB16

This figure shows schematically the construction of α-amylase-β-lactamase and penP-β-lactamase gene fusions. Several codons around the PstI sites are numbered. The line - - - indicates a fragment derived from pGK13-α-amylase; the line -.-.- a fragment derived from pRW101, the line —— a β-lactamase gene from pGPB11 and the line + + +, charged amino acid residues. For details, see Example V.

FIG. 5—constructions of plasmids pGPP3 and pGPP5

This figure shows the penP-penP and the α-amylase-penP gene fusions. In pGPP3 the original penP signal sequence encoding region is restored, whereas in pGPP5 a hybrid signal sequence region is constructed. For details, see Example V. The part indicated as -.-.- is derived from pRW101, and the part indicated as - - - from pGK13-α-amylase.

Figure 6:
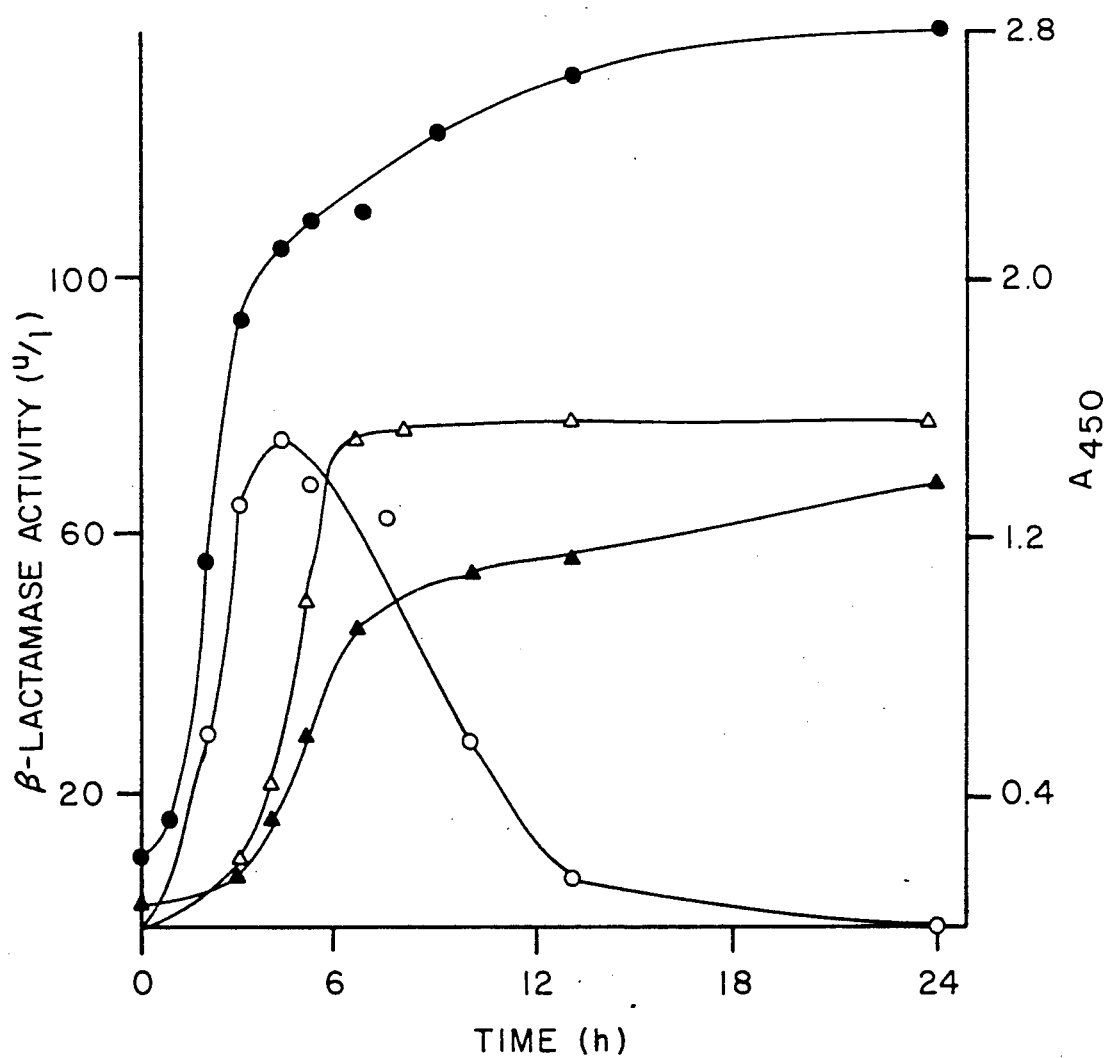

FIG. 6—Amounts of β-lactamase in the culture supernatant of 8G-5(pSPB8')

The recombinant bacteria (cf. Table 2) were grown in TY and in minimal medium. β-lactamase activities were determined with nitrocefin as described hereinafter on page 18. The growth of the bacteria was monitored by the absorbance at 450 nm. — — , $A_{450}$/TY; Δ-Δ-Δ, $A_{450}$/minimal medium; o-o-o, β-lactamase activity in TY medium; Δ-Δ-Δ, β-lactamase activity in minimal medium.

DESCRIPTION OF THE SPECIFIC EMBODIMENTS

Methods and compositions are provided for detecting signal sequences involved with secretion in unicellular microorganisms, particularly prokaryotic organisms. The methods are employed for identifying signal sequences present in the host genome, on the genome of other organisms and on other DNA fragments (identified or unidentified), evaluating such sequences, and then being able to isolate the sequences and use them with other than the wild-type gene to provide for efficient secretion of polypeptide sequences of interest, more particularly sequences foreign to the expression host. By employing the subject invention, the signal sequence can be detected and be evaluated with a plurality of genes other than the wild-type gene associated with the signal sequence. Efficient signal sequences discovered in this manner may then be utilized for secretion of products of interest, such as mammalian proteins, enzymes, both prokaryotic and eukaryotic, biocides, structural polymers, or the like.

The subject invention is exemplified by a determination of signal sequences in *Bacillus subtilis* as the screening host and *Escherichia coli* as the cloning host. While *E. coli* is found to be a particularly useful cloning host, and would be the host of interest for the cloning of DNA regardless of the source of the signal sequences, *Bacillus subtilis* may be considered exemplary of the Bacillis organisms, such as *B. thuringiensis, B. stearothermophilus, B. licheniformis,* as well as other prokaryotic organisms.

The method employs using vectors which serve for cloning and screening of genomic or cDNA for the presence of signal sequences, usually of unidentified fragments. The vectors are characterized by having a plurality of functional sequences. The vectors have at least one, usually two origins of replication, one for the expression host, preferably a Bacillus host, and the other for a cloning host, usually *E. coli*. The latter replication origin is for convenience. In a specific embodiment, a Bacillus host serves both the cloning and screening/expression functions. Usually, for the genomic screening, the replication system will be of a relatively low copy number, usually at least 1 and not more than about 500, more usually more than about 200 copy numbers. The copy number in the cloning host is primarily one of convenience, it is not of significance to this invention.

The vector optionally has 1 or more promoters, usually 0 to 1 promoter which is functional in the screening host. The presence of the promoter allows for detection of signal sequences which have been separated from their wild-type promoter, and for the detection of new signal sequences, namely coding for sequences which may act as secretory signal sequences but normally do not possess this activity. In this manner, relatively small fragments may be screened and the presence of the signal sequence detected. Furthermore, the efficiency of the signal sequence in providing for efficient production of the desired peptide will be separate from the efficiency of the promoter. However, since one can determine the amount of cytoplasmic peptide as compared secreted peptide, this ratio can be used to evaluate the efficiency of the signal sequence for secretion.

The next functional element in the vector, which may be the first functional element in the absence of the promoter, is a multiple cloning site (MCS). The MCS is characterized by having at least 2, usually at least 3, generally not more than 10, preferably not more than 6, restriction sites, at least 2 of which, and preferably all are unique to the vector. That is, the vector will be capable of being cleaved uniquely in the MCS. The cloning sites may be blunt ended or have overhangs of from 1 to 4 nucleotides, preferably having overhangs. Desirably, the overhangs will be capable of both, hybridizing with the overhangs obtained with restriction enzymes other than the restriction enzyme which cleaves at the restriction site in the MCS, and hybridizing with the overhangs obtained with the same restriction enzyme. While insertion of a fragment derived by restriction with a restriction endonuclease other than the restriction endonuclease employed for cleaving the vector will result in the inability to excise the insert, nevertheless, in some situations this may be desirable. In some instances this may allow for the use of smaller fragments by using a plurality of restriction endonucleases having different recognition sites or using restriction endonucleases which recognize four instead of six nucleotides.

The MCS will usually be not more than about 100 nucleotides, usually not more than about 60 nucleotides, and generally at least about 6 nucleotides, more usually at least about 10 nucleotides.

Desirably the MCS will be free of stop codons in the translational reading frame for the structural genes.

Where a convenient MCS is commercially available, the MCS may be modified by cleavage at a restriction site in the MCS and removal or addition of a number of nucleotides other than 3 or a multiple of 3, which results in a change in reading frame. In this manner, the reading frame will be changed so as to avoid termination of expression at a site internal to the MCS. Desirably, the MCS will be relatively free of codons which might interfer with the efficient secretion of the expression product. To that extent, at least 50% of the codons coded for by the MCS will code for neutral amino acids, desirably at least about 80%. Preferably, at least about 60% of the codons will be aliphatic, where the side chain may be polar, e.g. having an oxy, thio or amido functionality or non-polar, consisting solely of hydrogen and carbon. In addition, the MCS will usually be free of a processing signal.

In referring to a signal sequence, the signal sequence will normally have three regions. The first region will normally be a hydrophilic region, usually including one, more usually including at least about two positively charged amino acids, e.g. K or R. The charged region will usually be followed by a hydrophobic region, where the majority of the amino acids will be non-polar amino acids. The hyrophobic region will then be followed by a more polar region harboring the processing signal, which may involve two or more amino acids, which are recognized by a particular leader peptide enzyme which cleaves at the processing site. Processing signals may involve as many as eight amino acids or more an may be influenced by the amino acids present immediately adjacent to the processing site in the mature peptide.

The MCS may provide a chain of two or more amino acids between the genomic fragment and the expression product. Usually, the MCS will provide fewer than 30 amino acids, preferably fewer than about 20 amino acids. Of course, the number of amino acids introduced by the MCS will depend not only upon the size of the MCS, but also the site at which the genomic fragment is inserted into the MCS.

Joined to the MCS will be the expression product. The expression product may or may not include the C-terminal portion of a signal sequence or the wild-type processing signal associated with the expression product. Desirably, a plurality of expression products are employed in different vectors, where one vector may employ a gene having a processing signal and the other vector may employ a gene lacking a processing signal. In this manner, by comparing the resulting products, one can determine whether the fragment does or does not include an efficient processing signal.

The gene which is employed will have a number of constraints. One constraint is that the gene can be detected readily, either by detection of a metabolite, resistance to a biocide, e.g. antibiotic, or other means which allows for rapid screening of secretion of the expression product. For the most part, the expression product will be an enzyme, which produces a readily detectable metabolite, e.g. amylase, either $\alpha$- or $\beta$-amylase; which provides for protection from an antibiotic, e.g. $\beta$-lactamase, penicillinase, or bacteriocin. While it is feasable to screen the supernatant using various assays, e.g. immunoassays, Western blots, or the like, for detection of the expression product in the supernatant, preferably the expression product should allow for rapid screening and only after detection of positive clones will it usually be desirable to quantitate the amount of expression product in the supernatant. In addition, it will usually be of interest to determine the amount of cytoplasmic expression product. Since the cytoplasmic product will, for the most part, be unprocessed, it is desirable that the expression product be active, both with and without the N-terminal leader.

The expression product will be in reading frame with at least one, usually at least two of the restriction sites of the MCS. By being in reading frame is intended that upon cleavage of the fragment with the specified restriction endonucleases and insertion of the fragment in the complementary site of the MCS the gene will be in reading frame with the initiation codon of the fragment. Thus, by having a plurality of restriction sites, so that the genome may be cleaved with a plurality of restriction endonucleases, the probability of having the fragment and gene in reading frame to at least one site is greatly enhanced.

Finally, the vector may also include one or more markers. By marker is intended a gene capable of expression in the particular host which allows for ease of selection of those hosts containing the vector. The marker may provide resistance to a biocide, e.g. antibiotic, as described above, as well as other antibiotics, such as erythromycin, actinomycin, chloramphenicol, tetracycline, etc., complement auxotrophic hosts to provide prototrohpy, or the like. For each of the hosts involved, where the cloning and screening hosts require different markers, there will usually be two markers present. In this way, the clone may be rapidly screened to distinguish those clones which contain the vector and those clones which do not.

The genomic screening may be done with either a genomic library, that is a restriction endonuclease or sheared product from the chromosome and any extrachromosomal elements present in the host, or a cDNA library, where care must be taken to ensure that the sequence coding the N-terminal sequence has been obtained during reverse transcription and replication. The fragments which are employed will usually be at least about 45 bp, not more than about 5 kpb, usually not more than about 2 kpb and preferably at least about 60 bp. Since the fragments are random they may not only include the promoter and non-coding 5' sequence, but also the sequence encoding the signal sequence and processing signal and even portions of the mature expression product. The restricted fragments will be obtained with at least one restriction endonuclease, frequently a plurality of restriction endonucleases, where the restriction endonucleases may provide for the same or different overhangs or for blunt ended fragments.

A number of different techniques can be employed to control the size of the fragment. For example, one can use a restriction endonuclease providing a complementary overhang and a second restriction endonuclease to recognize a relatively common site, which provides a terminus which is not complementary to the terminus of the vector restriction site. After joining the fragments to the cleaved vector, one may further subject the resulting linear DNA to additional restriction enzymes, where the vector lacks recognition sites for such restriction enzymes. In this way, a variety of sizes can be obtained.

Where the vector provides a promoter, one can afford to use smaller fragments than when the vector does not provide the promoter. Thus, it will be desirable in many instances to either employ larger fragments or to have a promoter present in the vector which is upstream from the MCS and allows for transcription of the insert in conjunction with the expression product.

After the insert has been inserted into the vector and manipulated in and convenient manner, the vector may then be transformed into the cloning host. It may be desirable to provide for expression, as well, in the cloning host. In this instance, either the promoters of the genomic source will be functional in the cloning vector, or a promoter will be provided which provides for transcription of the expression construct in the cloning host. In this manner, one may in addition determine whether the signal sequences and processing signal is recognized by the cloning host, as well as the genomic source host. Thus, one can obtain some evidence of the presence of a signal sequence, since a positive result will be highly indicative of the presence of a signal sequence functional in the expression host, although not dispositive. Sometimes it may be desirable to clone and screen in the expression host. In such case, the vector comprising the insert may be transformed directly into the expression host.

Any technique may be used for introduction of the vector into the cloning host, as well as the screening host. Various techniques include conjugation, transformation, transfection, electroporation, fusion, or the like. The resulting transformants may then be grown in an appropriate nutrient medium providing for selection of those cloning hosts containing the vectors. The vectors may then be isolated and screened by transformation into an appropriate expression host and grown on a nutrient medium appropriate to the host. Efficient secretion may be determined by screening the supernatants for the presence of the secreted product. Thus, depending upon the nature of the expression product, various reagents may be added during or after growth which, for example, produce a detectable signal, e.g. a colored reaction, are lethal to the host in the absence of the secreted expression product, or the like. In this manner, one can rapidly screen a large number of clones for efficient secretion.

Those clones which appear to be promising may then be further analyzed in a variety of ways. The insert may be excised, using the flanking restriction sites, either those employed for insertion or those present in the MCS which were not employed and isolating the resulting fragment. This fragment may then be sequenced, so that the initiation codon and signal sequence may be determined, based on the coding characteristics. The protein product may be sequenced to determine the site at which processing occurred. The nucleic acid sequence may then be used as a probe to determine the wild-type gene which employs the particular signal sequence. The signal sequence may be isolated or it may be desirable to isolate a DNA sequence encoding the signal sequence and processing signal in conjunction with a few codons of the wild-type gene downstream from the processing signal. The extra codons may enhance secretion efficiency. In addition, one may obtain the promoter region and the non-coding sequence, which may be useful in enhancing transcription and translation of the product.

Employing the subject process, a number of previously undiscovered signal sequences were isolated and demonstrated to be active with genes other than the wild-type gene. These signal sequences encode for amino acid sequences as set forth in the Experimental section.

These signal sequences may be joined to any gene of interest for secretion, particularly in a Bacillus host. The sequences may be manipulated in a variety of ways. The 3' proximal sequence may be modified for introduction of a convenient restriction site if necessary. One or more codons may be added to the processing site to provide a convenient restriction site. Usually, the number of codons will be fewer than six, more usually fewer than five, generally at least two, where the codons may act in conjunction with nucleic acids present in the processing site for defining the recognition site. Where a restriction site is upstream from the processing site, an adapter can be prepared which would recreate the necessary codons encoding the processing site. In addition, the adapter may extend into the gene of interest, extending to a convenient restriction site and allowing for the entire construct to be in proper reading frame.

The various fragments may be ligated together in accordance with conventional ways to provide for an expression construct which results in efficient secretion and maturation of the final product. The expression product may be inserted into an appropriate vector, which may contain a transcriptional and translational initiation region, or such region may be associated with the signal sequence, so that the expression construct may include the necessary transcriptional and translational initiation and termination regions. Thus, the construct may be inserted into a vector which allows for replication and selection, as previously described.

A Bacillus host may be used for the production of a wide variety of products, both prokaryotic and eukaryotic. These products may include a variety of enzymes, such as prochymosin, α- and β-amylase, proteases, lipases, esterases, cellulases, mammalian proteins, which include growth factors, plasminogen activators, lymphokines, blood factors, interferons, colony stimulating factors, endorphins, serum albumins, hormones, and receptors.

By virtue of the subject invention, the products may be conveniently processed and secreted into the supernatant, where they may be isolated and purified.

In carrying out the subject invention, particular vectors were prepared. The specific embodiments, i.e. the construction of pGPA11, pGPB11 and pGPP11 is shown in FIG. 1. These vectors were constructed using the plasmids pHP12 and pHP14 (see FIG. 2) which are shuttle E. coli-B. subtilis vectors (4.2 kb, $Em^R$) containing the $Em^R$ gene from pGK13, the origin of replication and the lacZ region from pUC9 and pUC13, respectively, and a 1.6-kb fragment from the cryptic B. subtilis plasmid pTA1060 containing the replication functions.

Plasmid pGPA11 was constructed by inserting a 1.6 kb PstI-HindIII fragment from pGK13-α amy into PstI+HindIII digested pHP14. This fragment carries the α-amylase gene from B. licheniformis, but lacks the coding region for the first 26 N-terminal amino acid residues of the native signal peptide (29 amino acids in total). Therefore, this vector still contains the original processing site of the α-amylase gene.

Plasmid pGPP11 contains a 1.2 kb PstI-HindIII fragment form pRW101 carrying most of the penicillinase gene from B. licheniformis, but lacks the coding region for the first 13 N-terminal amino acids residues (the entire hydrophilic region) of the signal peptide. This fragment was fused to PstI+HindIII digested pHP14.

Plasmid pGPB11 was constructed by inserting into the HindIII site of pHP14 a 1.5 kb HindIII fragment carrying the E. coli β-lactamase gene from pKTH74 which lacks the entire signal sequence encoding region, including the original processing site.

In a specific embodiment of the invention these three recombinant vectors were used to isolate secretory signal coding regions, by shotgun cloning of restriction fragments of chromosomal *B. subtilis* DNA into the multicloning sites of the respective vectors. However, as can be seen in FIG. 3, in PGPA11, pGPB11 and pGPP11 the MCS contains an amber (TAG) nonsense codon (at the XbaI site) in reading frame with the structural genes. Since this limits the number of sites in the MCS which can be used for shotgun experiments, in another embodiment this amber codon was eliminated by digesting the plasmids with PstI, followed by removal of the 3' protruding sticky ends by T4 DNA polymerase. The resulting vectors were designated pGPA14, pGPB14, and pGPP14, respectively (see FIG. 3).

In still another embodiment of the invention, derivatives of plasmids pGPA14, pGPB14, and pGPP14 were constructed in which the 278 bp EcoRI fragment from pPL608, containing a SP02 phase promoter, was cloned into the unique EcoRI site of the MCS. It will be appreciated that any fragment derived from Bacillus phage SP02 DNA with transcriptional initiation activity may be used. These vectors have the advantage over the original ones in that they allow detection of additional secretory signal coding fragments, namely those which lack promoters.

The invention is further illustrated by the following examples which must be regarded as illustrations only, and in no way as limitations.

EXPERIMENTAL

Abbreviations Used $Amp^R$, ampicillin resistance; $Cm^R$, chloramphenicol resistance; $Em^R$, erythromycin resistance; $Km^R$, kanamycin resistance; MCS, multiple cloning site; bp, base pairs; kb, kilo base pairs.

Media and Plates

TY media contained (per liter): 10 g of tryptone, 5 g of yeast extract and 10 g of NaCl; pH 7.4. Minimal media used in the competence regimen for *B. subtilis* (8G-5) were as described by S. Bron and G. Venema, *Mutat. Res.* (1972) 15:1–10. Media used in protoplast transformation of *B. subtilis* were as described by S. Chang and S. N. Cohen, *Mol. Gen. Genet.* (1979) 168:111–115. Media were supplemented with selective antibiotics as follows: for *B. subtilis*: Cm, 5 µg/ml; Em, 1 µg/ml and for *E. coli*: Amp, 25 µg/ml; Em, 100 µg/ml; unless stated otherwise.

(Bio)Chemicals

Restriction enzymes, DNA polymerase I, T4 DNA polymerase, Bal 31, mung bean nuclease and T4 DNA ligase, obtained from Boehringer Mannheim (FRG), or from New England Biolabs (Beverly, Mass.), were used as recommended by the suppliers.

In the Examples, the general methods of analysis were conducted as follows.

Gel-Electrophoresis

Agarose gel-electrophoresis was carried out at 10 to 50 mA on 10 cm×6.5 cm×0.5 cm horizontal slab gels containing 0.8 to 2.0% agarose (Bio-Rad, Richmond, Calif.). Electrophoresis buffer consisted of 89 mM Tris-HCl, 89 mM boric acid, and 10 mM EDTA, pH 8.3. Ethidium bromide was added to 1 µg/ml to stain the DNA.

Assays for α-Amylase Activity a) In Solution.

i) The substrate solution in this case contained 60 mg Starch Azure (Sigma) which was suspended in 10 ml 20 mM potassium phosphate, pH 7.5, 50 mM NaCl, and heated for 1 min at 100° C. The mixture was centrifuged for 5 min at 5000 rpm and the pellet was resuspended in 10 ml 20 mM K-phosphate pH 7.5, 50 mM NaCl. Subsequently, 1.5 ml portions of the starch suspension were incubated with appropriate amounts of the enzyme solution and incubated for 10 to 60 min at 37° C. in a waterbath shaker (250 rpm). The reactions were stopped by centrifugation for 5 min at 5000 rpm in an Eppendorf centrifuge and then the absorbance at 595 nm of the supernatants was determined. One unit of α-amylase was defined as the amount of enzyme that increased the absorbance by 1.0 in 1 h at 37° C.

b) On Plates.

*E. Coli* colonies were grown on TY plates supplemented with 1% soluble starch. *B. subtilis* colonies were grown on minimal agar plates without glucose, supplemented with 1% soluble starch. After pouring iodine reagent (0.3% $I_2$+0.6% KI) on the plates, clear halos appeared around the α-amylase producing colonies.

c) In SDS-Polyacrylamide Gels

Sodium dodecyl sulfate-polyacrylamide (DSD-PAA) gel electrophoresis was performed on slab gels by the method of Laemmli (U.K. Laemmli, *Nature* (1970) 227:680–685). To detect α-amylase activity stacking and separating gels contained 0.25% soluble starch. After electrophoresis the gels were washed in 1.0M Tris/HCl pH 6.8+0.25% starch (four times for 30 min) in order to remove the SDS and allow renaturation of the proteins. Subsequently the gels were incubated for 2h at 65° C. (or overnight at 37° C.) in the same buffer. α-amylase activity was visualized as clear zones after the starch in the gels was stained blue with $I_2$ (0.5%) +KI (1.5%).

Assays for β-Lactamase Activity a) In Solution

β-lactamase activity in *B. subtilis* culture supernatants was determined spectrophotometrically using nitrocefin (Becton Dickinson B.V., Amersfoort, Netherlands) according to the method of C. H. O'Callaghan et al., *Antimicrob. Ag. Chemother.* (1972) 1:283–288. To prepare the substrate solution 5 mg nitrocefin was dissolved in 0.5 ml dimethylsulfoxide and subsequently diluted to 10 ml with 100 mM K-phosphate pH 7.0. Assay mixtures contained 0.3 ml of the substrate solution, 2.7 ml K-phosphate buffer pH 7.0 and an appropriate amount (25–500 µl) of the enzyme solution and were incubated for 5 to 10 min at room temperature. One unit of β-lactamase was defined as the amount of enzyme that increases the absorbance at 486 nm with 0.001 in 1 min at room temperature.

b) On Plates

*E. coli* colonies producing β-lactamase were selected directly by plating on TY agar supplemented with Amp (2 to 20 µg/ml).

*B. subtilis* colonies, which cannot be selected in this way, were plated on TY or minimal agar supplemented with 0.75% polyvinylalcohol. β-lactamase producing colonies were detected as those developing halos after the addition of iodine reagent (0.3% $I_2$+0.6% KI) for 1 min, followed by incubation with 5% penicillin G in 50 mM Na-phosphate, pH 6.4.

Originating Plasmids pKTH74: *E. coli* plasmid, 5.8 kb, $Amp^R$, $Tc^R$, described by I. Palva et al., *Proc. Natl. Acad. Sci. USA* (1982) 79:5582–5586.

pGK13: *Streptococcus cemoris* plasmid, derivative of pGK12 4.8 kb, $Cm^R$, $Em^R$, described by Kok et al. (1984), lab. collection, University of Groningen, the Netherlands.

pGK13-α-amylase: pGK13, carrying the α-amylase gene of *B. licheniformis*, 7.8 kb, $Cm^R$, $Em^R$, α-amylase+, lab. collection, University of Groningen, the Netherlands.

pRW101: bifunctional replicon, carrying the penicillinase gene of *B. licheniformis*, 7.0 kb, $Km^R$ (*B. subt.*), $Amp^R$ (*E. coli*), described by P.S.I. Mezes et al., *J. Biol. Chem.* (1983) 258:11211–11218.

pUC9: *E. coli* plasmid, 2.7 kb, $Amp^R$, described by J. Vieria and J. Messing *Gene* (1982) 19:259.

pUC13: *E. coli* plasmid, 2.7 kb, $Amp^R$, described by J. Messing, *Method Enzymol.* (1983) 101:20–78.

pPL608: *B. subtilis* plasmid, 5.0 kb, $Km^R$, $CM^R$, described by D. M. Williams et al. *J. Bacteriol.* (1981) 146:1162–1165.

pTA1060: cryptic *B. subtilis* plasmid, 7.8 kb, described by T. Uozumi et al., *J. Bacteriol.* (1980) 142:315–318.

EXAMPLE I

DNA Preparations

Chromosomal DNA was extracted from *B. subtilis* (8G-5) as described by S. Bron and G. Venema, *Mutat. Res.* (1972) 15:1–10. Preparative amounts of plasmid DNA were obtained according to the alkaline lysis procedure described by T. Maniatis et al., Molecular Cloning, a Laboratory Manual, Cold Spring Harbor Laboratory (1982) p. 90. Selected restriction fragments were obtained by separation on 0.8% or 2.0% agarose gels, followed by extraction and purification on DEAE NA-45 membranes (Schleicher & Schuell, Dassel, FRG) as indicated by the manufacturer. The analytical "miniprep" procedure described by D. Ish-Horowicz and J. F. Burke, *Nucl. Acids Res.* (1981) 9:2989–2998 was used to extract plasmids from 2.5 ml cultures of *E. coli*. Minipreps from *B. subtilis* were prepared according to the same procedure with the modification that before being lysed, the cells from 5 ml cultures were washed once by centrifugation with 50 mM Tris-HCl, pH 7.4, 10 mM EDTA, and 200 mM NaCl. Miniprep DNAs were incubated with 100μg/ml of pancreatic RNase (BDH, Poole, England) for 30 min at 37° C.

EXAMPLE II

Molecular Cloning Procedures

Vector molecules and restricted target DNAs were mixed in approximately a 1:2 weight ratio at a total concentration of 100 μg/ml.

For sticky end ligations the mixtures were heated for 5 min at 68° C. Buffer conditions were adjusted to 20 mM Tris-HCl, pH 7.6, 10 mM $MgCl_2$, 50 mM NaCl, 10 mM dithiothreitol (DTT), 1 mM ATP and 50 μg/ml bovine serum albumin (Boehringer Mannheim, FRG). Then approximately 0.2 U (for sticky end) or 1 U (for blunt end ligations) $T_4$ ligase was added. The ligation mixtures were incubated overnight at 4° C. (sticky ends) or overnight at room temperature (blunt ends). Ligated samples were used to transform *B. subtilis* or *E. coli* competent cells.

Filling in 3' recessed sticky ends was carried out by incubating the DNA (100 μg/ml) in 50 mM Tris-HCl, pH 7.2, 10 mM $MgSO_4$, 0.1 mM DTT, 50 μg/ml BSA with 1 U of the Klenow fragment of DNA polymerase I and 0.1 mM of the four dNTPs for 15 min at room temperature, or by incubating the DNA (100 μg/ml) with 1 U of T4 DNA polymerase for 30 min at 37° C. in a buffer containing 33 mM Tris-acetate pH 7.9, 66 mM K-acetate, 10 mM Mg-acetate, 0.5 mM DTT, 0.1 mg/ml BSA and 0.1 mM of the four dNTPs. 3' protruding termini were digested with T4 DNA polymerase under the same conditions. For partial digestions, the DNA (100 μg/ml) was incubated for 10 min. at 30° C. with 1U of Bal 31 in 20 mM Tris-HCl pH 9.1, 60 mM NaCl, 12 mM $CaCl_2$, 12 mM $MgCl_2$ and 1 mM EDTA. Bal 31-digested DNAs were treated with T4 DNA polymerase as described above and subsequently used for ligation.

In order to remove 5'-protruding sticky ends, DNA (100 μg/ml) was incubated for 25 min at 25° C. with 0.5 U mung bean nuclease in S1 buffer containing: 50 mM Na-acetate pH 4.6, 280 mM NaCl, 4.5 mM $ZnSO_4$ and 0.5% glycerol.

EXAMPLE III

Transformations

Portions of 0.1 ml of competent *B. subtilis* cells were exposed to 0.5 to 1 μg of plasmid DNA for 30 min at 37° C. in a waterbath shaker. To allow time for expression of antibiotic resistance markers, 0.1 ml of TY medium was added and the suspension was incubated for 1 h at 37° C. Transformants were selected on TY plates supplemented with selective antibiotics (Em, 1 μg/ml; Km, 5 μg/ml). Protoplasts of *B. subtilis* were transformed and regenerated as described by S. Chang and S. N. Cohen, *Mol. Gen. Genet.* (1979) 168:111–115. Transformed protoplasts were plated on DM3 medium containing Em (5 μg/ml). *E. coli* cells were made competent and were transformed with approximately 1 μg/ml of plasmid DNA by the $CaCl_2$/cold-shock procedure described by T. Maniatis et al., Molecular Cloning, A Laboratory Manual, Cold Spring Harbor Laboratory (1982) p. 250. After allowing time for expression of antibiotic resistance markers (1 h, 37° C.), transformants were selected on antibiotic-containing TY plates (Em, 200 μg/ml or Em, 50 μg/mo +Amp, 2 μg/ml).

EXAMPLE IV

Shotgun Cloning Procedures for Secretory Signals

*B. subtilis* chromosomal DNA was digested with Sau3A, AluI, HaeIII, or RsaI and subsequently ligated with BamHI or SmaI-digested vector molecules (pGPB14 or pGPA14) in a 4:1 weight ratio. Ligated samples were used to transform competent *E. coli* cells. Transformants were selected by plating on TY plates containing Em (200 μg/ml)+1% soluble starch (for pGPA14). Plasmid DNAs extracted from the transformants were subsequently used to transform competent *B. subtilis* cells with selection for Em (1 μg/ml). Transformants were analyzed for their capacity to secrete either α-amylase or β-lactamase into the culture medium as described hereinbefore on pages 17 and 18.

EXAMPLE V

Molecular Cloning of Known Secretory Signal Sequences

This Example shows the effects of fusion of the truncated genes to a number of known signal sequences in the correct reading frame, see FIGS. 4 and 5.

Purified BamH-PstI fragments from pRW101 and pGK13-α-amy were ligated with BamHI+PstI digested pGPB11. The 300 bp BamHI-PstI fragment from pRW101 contains the promoter and the coding region for the first 13 N-terminal amino acids of the penP signal peptide. The 940 bp BamHI-PstI fragment from pGK13-α-amy encodes the entire promoter and signal sequence, except for the last 3 amino acids, of α-amylase. Since $Amp^R$ transformants cannot be selected directly in B. subtilis ($Amp^R$ was defined as the ability of a single cell to form a colony on ampicillin-containing plates), ligation mixtures were used to transform E. coli BHB2600 cells. The construct pGPB15, in which the truncated β-lactamase gene is preceded by the promoter and signal sequence coding region of the α-amylase gene, yielded a considerable number of $Amp^R$ E. coli transformants. However, the fusion of the promoter and the hydrophilic part of the penP signal sequence coding region to the truncated β-lactamase gene (pGPB16) did not yield $Amp^R$ transformants in E. coli.

These results demonstrate that the appearance of $Amp^R$ transformants in E. coli was dependent on the fusion of a functional signal sequence to the truncated β-lactamase gene and that the secretion of β-lactamase was restored with the amy signal sequence. Moreover, since the wild-type precursor of β-lactamase is known to be inactive (P. C. Tai et al., Anal. Biochem. (1985) 144:199-203 and R. Roggenkamp et al., J. Biol. Chem. (1985) 260:1508-1512) the appearance of $Amp^R$ transformants (=β-lactamase activity) indicates that the hybrid protein is processed. Furthermore, these results support the observation that signal sequences may be functionally interchangeable (see also Example IX).

Also the experiments with pGPP3 (containing the original penP signal sequence) and pGPP5 (containing the original hydrophobic core of this signal extended with 15 extra amino acids, see for details FIG. 5) revealed that the hybrid signal sequence is functional in E. coli, cf. Table 1.

TABLE 1

Properties of Various Gene Fusions in B. subtilis and E. coli

| B. subtilis | | E. coli | |
|---|---|---|---|
| plasmids | halos on plates | plasmids | levels of resistance to Amp |
| pGPB14(SPO2) | — | pGPB14(SPO2) | 0 |
| pGPB14 | — | pGPB14 | 0 |
| pGPB15 | — | pGPB15 | $A_{20}$:100%,$A_{50}$:1% $A_{100}$:0.1% |
| pGPP11(SPO2) | + | pGPP11(SPO2) | "inoculum effect" |
| pGPP11 | — | pGPP11 | 0 |
| pGPP3 | +++ | pGPP3 | $A_{300}$:100% |
| pGPP5 | ++ | pGPP5 | $A_{20}$:100%,$A_{100}$:50% $A_{200}$:30%,$A_{300}$:20% |

B. subtilis cells containing various recombinant plasmids were analyzed for their ability to form halos on plates containing polyvinylalcohol as described on page 18. Overnight cultures of E. coli cells containing the various recombinant plasmids were plated on TY plates supplemented with increasing concentrations of ampicillin. The maximal ampicillin concentration tested was 300 μg/ml. The number of viable cells were expressed as percentage of those on non-selective plates. Plasmid pGPP11 shows a pronounced "inoculum effect" on the level of resistance that can be obtained. This means that a single cell is virtually defenseless against low concentrations of ampicillin, whereas the resistance level increases enormously when larger inocula are used.

From the results shown in Table 1 it appears that in contrast to the control (pGPB11), plasmid pGPB15 rendered E. coli cells resistant to rather high concentrations of Amp. However, in B. subtilis, neither 8G-5(pGPB15), nor 8G-5(pGPB14) showed the ability to form halos on polyvinylalcohol plates. The apparent lack of secretion of β-lactamase by B. subtilis is probably due to the breakdown of the secreted β-lactamase by extracellular proteases (K. Nakamura et al., Biochem. Biophys. Res. Comm. (1985) 128:601-606 and I. Ulmanen et al., J. Bacteriol (1985) 162:172-182. It is noteworthy that in contrast to E. coli cells that contain plasmid pGPP3, in which the original penP signal sequence was restored, E. coli cells containing pGPP5, in which the hybrid amylasepenP signal sequence preceded penP, are less resistant to Amp. This phenomenon which is also reflected by a decreased penicillinase production in B. subtilis, most likely can be explained by differences in secretory efficiencies of the two signal sequences.

EXAMPLE VI

Molecular Cloning of Unknown Export Signal Sequences

In order to minimize the risk of missing secretory signals by cloning the inserts in incorrect translational reading frames relative to the target genes a number of different restriction enzymes (Sau3A, AluI, HaeIII, RsaI) were used to cleave the B. subtilis 8G-5 chromosomal DNA. After shotgun cloning of B. subtilis DNA fragments into the various vectors, clones were selected in E. coli, either by their ability to form halos on starch plates (pSPA plasmids) or by their resistance to Amp (pSPB plasmids). Out of the thousands of colonies tested, α-amylase positive clones were obtained with efficiencies varying form 0.1 to 0.5% whereas $Amp^R$ clones were obtained about 5 times less efficiently (0.02–0.1%).

A random selection of 20 potential secretory-proficient clones is presented in Table 2. Restriction analysis showed that inserts of various lengths had been cloned. Moreover, the various inserts rendered the E. coli cells resistant to different concentrations of Amp. These results clearly demonstrate that this invention permits the isolation of many different secretory signal sequences.

TABLE 2

Properties of Potential Secretory-Proficient Clones Obtained in E. coli

| plasmid[1] | size of insert (bp)[2] | $Amp^R$ |
|---|---|---|
| pSPB4' | 710 | 10 |
| pSPB5' | 650 | 20 |
| pSPB6' | 790 | 10 |
| pSPB8' | 670 | 275 |
| pSPB9' | 360 | 150 |
| pSPB11' | 270 | 5 |
| pSPB12' | 830 | 10 |

TABLE 2-continued

Properties of Potential Secretory-Proficient Clones Obtained in E. coli

| plasmid[1] | size of insert (bp)[2] | Amp[R] |
|---|---|---|
| pSPB13' | 650 | 10 |
| pSPB16' | 790 | 50 |
| pSPB19' | 420 | 50 |
| pSPB20' | 1500 | 600 |
| pSPB21 | 740 | 50 |
| pSPB23 | 490 | 175 |
| pSPB28 | 280 | 190 |
| pSPB29 | 300 | 5 |
| pSPB30 | 260 | 5 |
| pSPB31 | 420 | 5 |
| pSPB32 | 1080 | 300 |
| pSPB34 | 370 | 10 |
| pSPB38 | 670 | 20 |

[1]The pSPB clones shown do not contain the SPO2 promoter.
[2]All pSPB clones contain Sau3A inserts. Since some of the pSPB clones contain partially digested Sau3A fragments, those inserts are redigested with Sau3A and religated into pGPB14 digested with BamHI. The new clones are indicated with a prime. The size of the inserts was determined by restriction analysis.

The level of resistance to Amp was defined as the maximal concentration of ampicillin to which 100% of the viable cells were resistant. This was determined as described in the legends to Table 1.

EXAMPLE VII

α-Amylase Activities Produced by the Recombinant Plasmids in B. subtilis

In order to prove that the selected inserts contain coding regions for secretory functions, a number of randomly chosen recombinant plasmids were transformed to competent B. subtilis cells and the transformants obtained were analyzed for α-amylase activities in the culture supernatants. The assays of the α-amylase activities (Table 3, page 29) show that considerable amounts of α-amylase activity could be detected in the culture supernatants of B. subtilis cells containing the recombinant plasmids. These results confirm the cloning of secretory signal sequence coding regions.

B. subtilis 8G-5(pSPA2, pSPA8, pSPA12) and pSPA13 exhibited α-amylase activities which were substantially higher than those produced by B. subtilis (pGK13-α-amylase) i.e., the plasmid containing the native α-amylase secretory signal sequence. Since all α-amylase positive transformants were selected with a vector containing the SPO2 promoter, the inserts do not necessarily contain promoter activity. Deletion of the SPO2 promoter in pSPA8, pSPA9, pSPA12, and pSPA42 revealed (Table 3) that some inserts contain promoter activity (pSPA8, pSPA9, pSPA12) and others do not (pSPA42).

This observation clearly shows that secretory functions can be selected with a higher efficiency by using selection vectors which contain a promoter sequence upstream of the site used for insertion of target DNA.

The plasmids pSPA2, pSPA8, and pSPA12 were deposited in Bacillus subtilis strain 8G-5 on May 2, 1986 under the provisions of the Budapest Treaty with the Centraalbureau voor Schimmelcultures, Oosterstraat 1, NL-3742 SK Baarn, and were allotted the numbers CBS 248.86, CBS 249.86, and CBS 250.86, respectively.

TABLE 3

Amounts of α-Amylase in the Culture Supernatants of Various B. subtilis Clones

| plasmid[1] | size of insert (bp)[2] | α-amylase activity in the culture supernatant (U/ml) of B. subtilis |
|---|---|---|
| pSPA2[3] | 730 | 525 |
| pSPA8[3] | 340 | 345 |
| pSPA8(−SPO2) | 340 | 175 |
| pSPA9 | 1400 | 45 |
| pSPA9(−SPO2) | 1400 | 2 |
| pSPA12[3] | 700 | 270 |
| pSPA12(−SPO2) | 700 | 15 |
| pSPA13 | 1200 | 150 |
| pSPA26 | 210 | 3 |
| pSPA31 | 50 | 60 |
| pSPA42 | 400 | 4 |
| pSPA42(−SPO2) | 400 | 0 |
| pGPA14 | | 0 |
| pGK13-α-amylase | | 100 |

[1]All pSPA clones shown contain the SPO2 promoter, except where otherwise stated.
[2]pSPA2 contains an AluI insert, pSPA8 contains a HaeIII insert, and pSPA9, 12, 13, 26, 31, and 42 contain a RsaI insert.
[3]The plasmids pSPA2, pSPA8, and pSPA12 were deposited with CBS under Nos. 248.86, 249.86, and 250.86, respectively.

The B. subtilis cells were grown for one day in TY medium and the α-amylase activities in the culture supernatants were determined as described hereinbefore on page 17.

EXAMPLE VIII

β-Lactamase Activities Produced by the Recombinant Plasmids in B. subtilis

A comparative study was made on the β-lactamase activities in the culture supernaturants of B. subtilis cells (strain 8G-5) carrying various recombinant plasmids, either on polyvinylalcohol plates or by the nitrocefin assay, after growing the cells overnight in rich media. However, significant β-lactamase activity could not be detected by using these methods. This result is in accordance with the results described in Example V for 8G-5(pGPB15). Most likely the absence of activity is caused by the sensitivity of the β-lactamase to the B. subtilis exo-proteases. (K. Nakamura et al., Biochem. Biophys. Res. Comm. (1985) 128:601–606, I. Ulmanen et al., J. Bacteriol. (1985) 162:172–182, I Palva et al., Proc. Natl. Acad Sci. U.S.A. (1982) 79:5582–5586). This could be demonstrated by an investigation of the β-lactamase production in minimal versus rich media (see FIG. 6). In TY medium, the amount of β-lactamase increases during the logarithmic and early stationary phases of growth.

However, the amount of β-lactamase was decreasing after prolonged growth and was completely lost in overnight cultures. In contrast, the amount of β-lactamase remained constant up to 24 h in minimal medium. These results support the idea that, at least in TY medium, β-lactamase is unstable, probably due to proteolysis.

The amount of β-lactamase in the supernatant of some pSPB clones is given in Table 4.

TABLE 4

Amounts of β-Lactamase in the Culture Supernatants of Various B. subtilis clones

| Plasmid | B. subtilis β-lactamase activity (U/ml) |
|---|---|
| pSPB4' | 630 |

TABLE 4-continued

Amounts of β-Lactamase in the Culture
Supernatants of Various B. subtilis clones

| Plasmid | B. subtilis β-lactamase activity (U/ml) |
|---|---|
| pSPB8' | 800 |
| pSPB9' | 16 |
| pSPB19' | 230 |
| pSPB20' | 585 |
| pSPB23 | 9 |
| pSPB28 | 17 |
| pSPB32 | 78 |

The amount of β-lactamase was determined in minimal medium as described hereinbefore on page 18.

EXAMPLE IX

The Interchangeability of the Cloned Secretory Signals

This example shows that the secretory signal sequences detected with pGA14 are functional in pGPB14 and vice versa (See Table 5). Most constructed pSPB-A vectors, containing the β-lactamase gene preceded by inserts derived from pSPA clones conferred resistance to ampicillin in E. coli. Moreover, the same plasmids produced considerable levels of β-lactamase activity in B. subtilis. Furthermore, the pSPA-B clones, in which the α-amylase gene is preceded by inserts originally selected in pGPB14, produced and secreted α-amylase (see Table 5).

However, a comparison of Tables 5 and 3 show that in B. subtilis, the relative order of the levels of α-amylase activities with the orogonal pSPA vectors (Table 3) and those of the β-lactamase with the interchanged pSPB-A vectors (Tables 5) were not identical. Qualitatively similiar results were obtained in the reciprocal experiment (Tables 5 and 4). Since in this comparison no differences at the transcriptional and translational level existed, and the same secretory signals were used, these results suggest that the efficiency of protein secretion in B. subtilis was affected both by the nature of the secretory signal sequences as well as by the mature parts of the proteins.

Furthermore, the levels of β-lactamase activities in the supernatants of B. subtilis cells containing pSPB-A vectors (see Table 5) were, on average, higher (sometimes even 10-30 times) than those in supernatants of B. subtilis cells containing pSPB vectors (see Table 4). Moreover, the pSPA vectors generally gave slightly higher levels of α-amylase than the pSPA-B vectors.

In conclusion, these results show that all the cloned secretory signal sequences tested were functionally interchangeable between the various vectors and the results suggest that with the two probe vectors different "classes" secretory signals have been picked up.

TABLE 5

Interchangeability of Secretory Signals

| Plasmid | E. coli amp$^r$ | B. subtilis β-lactamase activity U/ml | Plasmid | B. subtilis α-amylase activity U/ml |
|---|---|---|---|---|
| pSPB-A2 (−SPO2) | 175 | 27,000 | pSPA-B4' | 123 |
| pSPB-A2 (+SPO2) | 300 | 20,000 | pSPA-B8' | 16 |
| pSPB-A8 (−SPO2) | 300 | 495 | pSPA-B9' | 5 |
| pSPB-A9 (+SPO2) | 300 | 2900 | pSPA-B19' | 0.6 |
| pSPB-A12 (−SPO2) | 10 | 34 | pSPA-B20' | 20 |
| pSPB-A13 (−SPO2) | 300 | 4200 | pSPA-B23 | 3.8 |
| pSPB-A13 (+SPO2) | 300 | 1600 | pSPA-B28 | 37 |
| pSPB-A26 (+SPO2) | 0 | 880 | pSPA-B32 | 96 |
| pSPB-A31 (+SPO2) | 100 | 720 | pSPA-B9' (+SPO2) | 82 |
| pSPB-A42 (+SPO2) | 20 | 710 | pSPA-B19' (+SPO2) | 12 |
| | | | pSPA-B20' (+SPO2) | 40 |
| | | | pSPA-B23 (+SPO2) | 57 |

The amp$^r$ level of E. coli cells was determined as described in the legends of Tables 1 and 2.

β-lactamase activities of B. subtilis cells were determined with nitrocefin as described hereinbefore on page 18. α-amylase activities of B. subtilis cells were determined as described herein on page 17.

EXAMPLE X

Secretion Versus Lysis

The results presented in the previous Examples clearly demonstrate that the vectors pGPB14 and pGPA14 can be used to select for secretory coding regions, which function both in E. coli and in B. subtilis. To exclude the possibility that the enzymatic activities measured in B. subtilis were the result of cell lysis rather than of secretion, the cellular location of α-amylase produced by pSPA2 and pSPA8 was compared with the location of a cytoplasmic marker protein, for which isocitrate dehydrogenase (ICDH) was chosen. At first it was tested whether ICDH itself was stable in various media (see Table 6). After 24 h of incubation at 37° C. in minimal medium or in the supernatant of a B. subtilis overnight culture in this medium, 80% of the original ICDH activity was still present. However, when incubated in TY medium the activity was completely lost after 3 to 5 hr at 37° C.

TABLE 6

Stability of Isocitrate Dehydrogenase (ICDH) Activity in Various Media

| time (h) | TY medium | supernatant (TY medium) | minimal medium | supernatant (minimal medium) |
|---|---|---|---|---|
| 0 | 100 | 100 | 100 | 100 |
| 1 | 75 | 77 | 123 | 100 |
| 2 | 40 | 34 | 116 | 126 |
| 3 | 14 | 15 | 116 | 125 |
| 5 | 0 | 0 | 118 | 126 |
| 24 | 0 | 0 | 76 | 84 |

10 ml portions of an overnight culture of B. subtilis strain 8G-5 (or DB104) in either TY, or minimal medium were centrifuged for 10 min at 6000 rpm. The cells were washed twice by centrifugation. The pellets were resuspended in 5 ml starvation medium, containing 200 μg/ml lysozyme, and incubated for 15 min at 37° C. 2.5 ml portions of the lysed cells were substantially mixed with 2.5 ml portions of either TY medium, supernatant of a TY culture, minimal medium or culture supernatant of a culture grown in minimal, and incubated at 37° C. As a function of time the ICDH activities are given as percentages of the original ICDH activity.

Similiar results were obtained with supernatants of *B. subtilis* culture of 8G-5 and DB104 (protease deficient strain, F. Kawamura and R. H. Doi, *J. Bacteriol.* (1984) 160:442–444.) These results indicate that ICDH can be used as a cytoplasmic marker in minimal, but not in TY medium.

Table 7 shows that the α-amylase activity was predominantly found in the culture supernatants whereas most if not all of the ICDH activity was associated with the cell pellets. These results strongly support the conclusion that the α-amylase activities measured in the supernatants were the result of secretion rather than of cell lysis.

TABLE 7

α-Amylase and ICDH Activities in Cell Pellets and Culture Supernatants of Two *B. subtilis* Clones

| plasmid | α-amylase activity (U/ml) | | ICDH activity (U/ml) | |
|---|---|---|---|---|
| | supernatant | pellet | supernatant | pellet |
| pSPA2 | 100 | 1 | 3.9 | 287 |
| pSPA8 | 83 | 8 | 23 | 122 |

Cultures were grown overnight in minimal medium without glucose. 1 ml portions were centrifuged for 3 min in an Eppendorf centrifuge. The cells were washed twice with 100 mM K-phosphate, pH 8.0. The pellets were suspended in 0.5 ml 100 mM K-phosphate, pH 8.0, 200 μg/ml lysozyme and incubated for 15 min at 37° C. The culture supernatants were filtered through a 0.45 μm filter in order to remove cells and debris. Subsequently, the α-amylase and ICDH activities were determined.

EXAMPLE XI

α-Amylase Activities in SDS-Polyacrylamide Gels

The distribution of α-amylase activity in culture supernatants in cell pellets of a number of pSPA clones on SDS-polyacrylamide (PAA) gels was examined. Purified α-amylase from *B. licheniformis* was used as a control to determine the molecular weight position of the mature α-amylase. The molecular weight positions of the α-amylases isolated from the culture supernatants of 8G-5(pGK13-amy) and 8G-5(pSPA2, pSPA8, pSPA9) seemed to be identical to that of the control indicating that in all constructs cleavage of the secretory function had occurred at about the same processing site of α-amylase. Extracts of cell pellets from 8G-5(pSPA2 and pSPA8) showed α-amylase bands at higher molecular weight positions than found in the supernatants. The presursor in 8G-5(pSPA2) is of higher molecular weight than that expressed in 8G-5(pSPA8). It would appear that some of the precursor forms of the *B. licheniformis* α-amylase are enzymatically active. Since the precursor bands could be detected immunologically as well as enzymatically with the same intensities relative to the mature products, it would appear that the specific activity of the precursor forms is similiar to that of the mature product. Since in 8G-5(pSPA2, pSPA8) under steady state conditions precursor forms could be detected, the rate of secretion and/or processing of the α-amylase in these fusions appears to be delayed as compared to the wild-type. No precursor forms could be detected in the cell pellets of 8G-5(pSPA9, pSPA12, pSPA13) in the gels.

EXAMPLE XII

The Cell Associated α-Amylase and β-Lactamase

The amount of α-amylase activity associated with the cell pellets was determined. The results are shown in the following table.

TABLE 8

| Cell-Associated Enzymatic Activities | | |
|---|---|---|
| Plasmid | | % cell-associated α-amylase activity |
| pSPA2 | (+SPO2) | 0.6 |
| pSPA8 | (+SPO2) | 14 |
| pSPA9 | (+SPO2) | 6 |
| pSPA12 | (−SPO2) | 1.3 |
| pSPA13 | (+SPO2) | 1.4 |
| pSPA26 | (+SPO2) | 73 |
| pSPA31 | (+SPO2) | 2.5 |
| pSPA42 | (+SPO2) | 12 |
| pSPA-B4' | (−SPO2) | 4 |
| pSPA-B8' | (−SPO2) | 13 |
| pSPA-B9' | (−SPO2) | 1 |
| pSPA-B9' | (+SPO2) | 2 |
| pSPA-B19' | (−SPO2) | 0 |
| pSPA-B19' | (+SPO2) | 2 |
| pSPA-B20' | (−SPO2) | 21 |
| pSPA-B20' | (+SPO2) | 17 |
| pSPA-B23 | (−SPO2) | 33 |
| pSPA-B23 | (+SPO2) | 19 |
| pSPA-B28 | (−SPO2) | 2 |
| pSPA-B32 | (−SPO2) | 1 |
| pGK13-amy | | 0 |

*B. subtilis* cells were grown overnight in TY medium. α-amylase activities in supernatants and cell pellets were determined as described hereinbefore on page 17.

In cells with pGK13-amy, containing the wild-type α-amylase gene, no activity could be detected in extracts of the cell pellets. With the exception of 8G-5(pSPA-B19'), reproducible amounts of α-amylase activity were associated with the cell pellets. As evidenced by the above results, a number of plasmids provide relatively large amounts of cell associated α-amylase. In the presence of the SPO2 promoter, the amounts of the α-amylase activities in the supernatants of *B. subtilis* cultures containing the various plasmids were increased. Despite this increase, the relative amount of cell-associated α-amylase was not altered.

EXAMPLE XIII

Secretory Signal Sequences of Various Recombinant Plasmids

Inserts of pSPB4' to pSPB20', pSPB21 to pSPB38 and pSPA2 to pSPA42 were sequenced according to the dideoxy method of Sanger and analyzed for the presence of secretory signal sequences. By matching the three reading frames with the known reading frame of α-amylase or β-lactamase, the proper reading frame was determined. Consequently, the length of the precursor (the secretory signal sequence plus mature enzyme) was compared with data obtained with an in vitro transcription-translation system in order to support the validity of the sequence. The following table indicates a number of the sequences.

TABLE 9

| Insert Of | Sequence |
|---|---|
| pSPA2 | Met arg+ lys+ ser leu ile thr leu gly leu ala ser val ile gly thr ser ser phe leu ile pro phe thr ser lys+ thr ala ser ala glu− thr leu asp− glu− lys+ lys+ gln lys+ ile glu− ser lys+ gln ser glu− val ala ser ser ile glu− ala lys+ glu− lys+ glu− leu thr glu− ∫* gly asp− pro leu glu− ser thr ala ala ala |
| pSPA8 | Met lys+ lys+ met leu val val leu leu phe ser ala leu leu leu asn gly cys gly ser gly glu− ser lys+ ala asn thr ala glu− thr pro glu− val leu asp− val lys+ leu thr gly ∫ gly asp− pro leu glu− ser thr ala ala ala |
| pSPA12 | Met ile arg+ gly ile leu ile ala val leu gly ile ala ile val gly ∫ gly asp− pro leu glu− ser thr ala ala ala |
| pSPA13 | Met leu lys+ lys+ val ile leu ala ala phe ile leu val gly ser ∫ gly asp− pro leu glu− ser thr ala ala ala |
| pSPA26 | Met ser gln gln his+ asp− tyr val ile gly lys+ asn ala val ile glu− thr leu lys+ ser asp− arg+ leu asp− leu phe pro leu leu arg+ leu thr lys+ lys+ pro lys+ val gln thr gly ile asp− thr leu leu pro asp− tyr lys+ lys+ gln ∫ glu asp− pro leu glu+ ser thr ala ala ala |
| pSPA31 | Met asp− glu− val his+ glu− glu− glu− \|** glu− phe glu− leu ala pro gly leu phe ile leu leu phe leu phe val met ala val ile gly∫ gly asp− pro leu glu− ser thr ala ala ala |
| pSPA42 | Met leu lys+ arg+ thr ser phe val ser ser leu phe ile ser ser ala val leu leu ser ile leu leu pro ser gly leu ser his+ thr leu ser ala lys+ gly thr asn lys+ asn asn leu phe phe phe asp− thr glu− thr thr gly leu gly gly gly ala gly asn thr ile phe leu leu gly his+ ala arg+ val tyr glu− asp− arg+ val thr val lys+ gln his+ leu leu pro lys+ pro gly asn glu− val ala leu tyr gln ser phe leu ser glu− val asp− ile thr ser leu val thr tyr asn gly lys+ ala phe asp− thr ∫ gly asp− pro leu glu− ser thr ala ala ala |
| pSPB4' | Met lys+ ile ser arg+ ile leu leu ala ala val ile leu ser ser val phe ser ile thr tyr leu gln ser asp− leu gly trp phe ala lys+ glu− gly gln met asp− glu− thr phe thr lys+ ala ala phe lys+ leu lys+ thr gly glu− val ser asp− ∫ pro leu glu− ser thr ala gln ala cys |
| pSPB9' | Met lys+ gln thr val leu leu leu phe thr ala leu phe leu ser gly cys ser val ala ser ala asp− asp− ser val pro arg+ phe thr glu− glu− gly lys+ tyr ile gly ser ala asp− ∫ pro leu glu− ser thr ala gln ala cys |
| pSPB19' | Met lys+ lys+ leu val phe gly leu leu ala ile val leu phe gly cys gly leu tyr ile tyr his+ val trp phe gly asp− ∫ pro leu glu− ser thr ala gln ala cys |
| pSPB20' | Met leu lys+ lys+ cys ile leu leu val phe leu cys val gly leu ile gly leu ile gly cys ser lys+ thr asp− ser pro glu− asp− ∫ pro leu glu− ser thr ala gln ala cys |
| pSPB23 | Met arg+ lys= trp ile ala ala ala gly leu ala tyr val leu tyr gly leu phe phe tyr trp tyr phe phe leu ser gly asp− set ala ile pro glu− ala val lys− gly thr gln ala asp− ∫ pro leu glu− ser thr ala gln ala cys |
| pSPB28 | Met pro ile lys+ lys+ lys+ val met met cys leu ala val thr leu val phe gly ser met ser phe pro thr leu thr asn ser gly gly phe lys+ glu− ser thr asp− ∫ gly asp− pro leu glu− ser thr ala gln ala cys |
| pSPB32 | Met lys+ leu val pro arg+ phe arg+ lys+ gln trp phe ala tyr leu thr val leu cys leu ala leu ala ala ala val ser phe gly val pro ala lys+ ala ala glu− asn pro gln thr ser val ser asn thr gly lys+ glu− ala asp− ala thr lys+ asn gln thr ser lys+ ala asp− ∫ pro leu glu− ser thr ala gln ala cys |

*The amino acids behind this line ∫ are from the multiple cloning site of the plasmid.
**The amino acids before this | line are from the SPO2 fragment.

By using hydrophobicity plotting of Hopp and Woods, *Proc. Natl. Acad. Sci. U.S.A.* (1981) 78:3824–3828, it was demonstrated that most secretory signals have a hydrophilic head (positively charged) and a hydrophobic core. Several of the secretory signal sequences, e.g., pSPA2, pSPA26, pSPA42, pSPB32, and pSPB41, differ from signal sequences which are known from the literature as being significantly longer. A number of those sequences improve secretion as demonstrated with pSPA2.

As is evidenced by the above results, the subject method provides for a convenient and efficient system for isolating signal sequences from hosts and evaluating their efficiency in a rapid and convenient manner. The signal sequences may then be employed with a wide variety of genes other than the wild-type, to provide for efficient production of an open reading frame of interest. In this manner, a variety of hosts, particularly unicellular microorganism hosts, more particularly prokaryotic hosts, may be screened to identify the sequences which may find use for the production of various peptides in unicellular microorganisms.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A DNA sequence which encodes a secretory sequence comprising an amino acid sequence selected from the group consisting of:

Met arg lys ser leu ile thr leu gly leu ala ser val ile gly thr ser ser phe leu ile pro phe thr ser lys thr ala ser ala gly thr leu asp gly lys lys gln lys ile gly ser lys gln ser gly val ala ser ser ile gly ala lys gly lys leu thr glu;

Met lys lys met leu val val leu leu phe ser ala leu leu leu asn gly cys gly ser gly glu ser lys ala asn thr ala gly thr pro gly val ley asp val lys leu thr gly;

Met ile arg gly ile leu ile ala val leu gly ile ala ile val gly;

Met leu lys lys val ile leu ala ala phe ile leu val gly ser;

Met ser gln gln his asp tyr val ile gly lys asn ala val ile glu thr leu lys ser asp arg leu asp leu phe pro leu leu arg leu thr lys lys pro lys val gln thr gly ile asp thr leu leu pro asp tyr lys lys gln;

glu phe glu leu ala pro gly leu phe ile leu leu phe leu phe val met ala val ile gly;

Met leu lys arg thr ser phe val ser ser leu phe ile ser ser ala val leu leu ser ile leu leu pro ser gly leu ser his thr leu ser ala lys gly thr asn lys asn asn lue phe phe phe asp thr glu thr thr gly leu gly gly gly ala gly asn thr ile phe leu leu gly his ala arg val tyr gly asp arg val thr val lys gln his leu leu pro lys pro gly asn gly val ala leu tyr gln ser phe leu ser glu val asp ile thr ser leu val thr tyr asn gly lys ala phe asp tyr;

Met lys ile ser arg ile leu leu ala ala val ile leu ser ser val phe ser ile thr tyr leu gln ser asp leu gly trp phe ala lys glu gly gln met asp glu thr phe thr lys ala ala phe lys leu lys thr gly glu val ser asp;

Met lys gln thr val leu leu leu phe thr ala leu phe leu ser gly cys ser val ala ser ala asp asp ser val pro arg phe thr glu glu gly lys tyr ile gly ser ala asp;

Met lys lys leu val phe gly leu leu ala ile val leu phe gly cys gly leu tyr ile tyr his val trp phe gly asp;

Met leu lys lys cys ile leu leu val phe leu cys val gly leu ile gly leu ile gly cys ser lys thr asp ser pro glu asp;

Met arg lys trp ile ala ala ala gly leu ala tyr val leu tyr gly leu phe phe tyr trp tyr phe phe leu ser gly asp set ala ile pro glu ala val lys gly thr gln ala asp;

Met pro ile lys lys lys val met met cys leu ala val thr leu val phe gly ser met ser phe pro thr leu thr asn ser gly gly phe lys glu ser thr asp; and Met lys leu val pro arg phe arg lys gln trp phe ala tyr leu thr val leu cys leu ala leu ala ala ala val ser phe gly val pro ala lys ala ala gly asn pro gln thr ser val ser val ser asn thr gly lys glu ala asp ala thr lys asn gln thr ser lys ala asp.

2. A DNA sequence which encodes an amino acid sequence comprising a sequence selected from the group consisting of:

Met arg lys ser leu ile thr leu gly leu ala ser val ile gly thr ser ser phe leu ile pro phe thr ser lys thr ala ser ala gly thr leu asp gly lys lys gln lys ile glu ser lys gln ser glu val ala ser ser ile glu ala lys glu lys glu leu thr glu;

Mey lys lys met leu val val leu leu phe ser ala leu leu leu asn gly cys gly ser gly glu ser lys ala asn thr ala glu thr pro glu val leu asp val lys leu thr gly;

Met ile arg gly ile leu ile ala val leu gly ile ala ile val gly;

Met leu lys lys val ile leu ala ala phe ile leu val gly ser;

Met ser gln gln his asp tyr val ile gly lys asn ala val ile gly thr leu lys ser asp arg leu asp leu phe pro leu leu arg leu thr lys lys pro lys val gln thr gly ile asp thr leu leu pro asp tyr lys lys gln;

gly phe glu leu ala pro gly leu phe ile leu leu phe leu phe val met ala val ile gly;

Met leu lys arg thr ser phe val ser ser leu phe ile ser ser ala val leu leu pro ser gly leu ser his thr leu ser ala lys gly thr asn lys asn asn leu phe phe phe asp thr glu thr thr gly leu gly gly gly ala gly asn thr ile phe leu leu gly his ala arg val tyr gly asp arg val thr val lys gln his leu leu pro lys pro gly asn gly val ala leu tyr gln ser phe leu ser glu val asp ile thr ser leu val thr tyr asn gly lys ala phe asp tyr;

Met lys ile ser arg ile leu leu ala ala val ile leu ser ser val phe ser ile thr tyr leu gln ser asp leu gly trp phe ala lys glu gly gln met asp glu thr phe thr lys ala ala phe lys leu lys thr gly glu val ser asp;

Met lys gln thr val leu leu leu phe thr ala leu phe leu ser gly cys ser val ala ser ala asp asp ser val pro arg phe thr glu glu gly lys tyr ile gly ser ala asp;

Met lys lys leu val phe gly leu leu ala ile val leu phe gly cys gly leu tyr ile tyr his val trp phe gly asp;

Met leu lys lys cys ile leu leu val phe leu cys val gly leu ile gly leu ile gly cys ser lys thr asp ser pro glu asp;

Met arg lys trp ile ala ala ala gly leu ala tyr val leu tyr gly leu phe phe tyr trp tyr phe phe leu ser gly asp set ala ile pro glu ala val lys gly thr gln ala asp;

Met pro ile lys lys lys val met met cys leu ala val thr leu val phe gly ser met ser phe pro thr leu thr asn ser gly gly phe lys glu ser thr asp; and Met lys leu val pro arg phe arg lys gln trp phe ala tyr leu thr val leu cys leu ala leu ala ala ala val ser phe gly val pro ala lys ala ala glu asn pro gln thr ser val ser asn thr gly lys glu ala asp ala thr lys asn gln thr ser lys ala asp.

3. A DNA sequence which encodes an amino acid sequence to claim 2, wherein selected from the group consisting of:

Met arg lys ser leu ile thr leu gly leu ala ser val ile gly thr ser ser phe leu ile pro phe thr ser lys thr ala ser ala gly thr leu asp glu lys lys gln lys ile glu ser lys gln ser glu val ala ser ser ile glu ala lys glu lys glu leu thr glu;

Met lys lys met leu val val leu leu phe ser ala leu leu leu asn gly cys gly ser gly glu ser lys ala asn thr ala glu thr pro glu val leu asp val lys leu thr gly;

Met ile arg glu ile leu ile ala val leu gly ile ala ile val gly;

Met leu lys lys val ile leu ala ala phe ile leu val gly ser;

Met ser gln gln his asp tyr val ile gly lys asn ala val ile glu thr leu lys ser asp arg leu asp leu phe pro leu leu arg leu thr lys lys pro lys val gln thr gly ile asp thr leu leu pro asp tyr lys lys gln;

glu phe glu leu ala pro gly leu phe ile leu leu phe leu phe val met ala val ile gly;

Met leu lys arg thr ser phe val ser ser leu phe ile ser ser ala val leu leu ser ile leu leu pro ser gly leu ser his thr leu ser ala lys gly thr asn lys asn asn leu phe phe phe asp thr glu thr gly leu gly gly gly ala gly
asn thr ile phe leu leu gly his ala arg val tyr gly asp
arg val thr val lys gln his leu leu pro lys pro gly asn
glu val ala leu tyr gln ser phe leu ser glu val asp ile
thr ser leu val thr tyr asn gly lys ala phe asp tyr;

Met lys ile ser arg ile leu leu ala ala val ile leu ser ser
val phe ser ile thr tyr leu gln ser asp leu gly trp phe
ala lys glu gly gln met asp gly thr phe thr lys ala ala
phe lys leu lys thr gly glu val ser asp;

Met lys gln thr val leu leu leu phe thr ala leu phe leu
ser gly cys ser val ala ser ala asp asp ser val pro art
phe thr glu glu gly lys tyr ile gly ser ala asp;

Met lys lys leu val phe gly leu leu ala ile val leu phe
gly cys gly leu tyr ile tyr his val trp phe gly asp;

Met leu lys lys cys ile leu leu val phe leu cys val gly
leu ile gly leu ile flu cys ser lys thr asp ser pro glu
asp;

Met arg lys trp ile ala ala ala gly leu ala tyr val leu tyr
gly leu phe phe tyr trp tyr phe phe leu ser gly asp
ser ala ile pro glu ala val lys gly thr gln ala asp;

Met pro ile lys lys lys val met met cys leu ala val thr
leu val phe gly ser met ser phe pro thr leu thr asn
ser gly gly phe lys glu ser thr asp; and Met lys leu val pro arg phe arg lys gln trp phe ala tyr
leu thr val leu cys leu ala leu ala ala ala val ser phe
gly val pro ala lys ala ala glu asn pro gln thr ser val
ser asn thr gly lys glu ala asp ala thr lys asn gln thr
ser lys ala asp.

4. A DNA construct comprising a first DNA sequence in proper reading frame with a second DNA sequence encoding an amino acid sequence capable of functioning as a secretory signal sequence wherein said second DNA sequence is a heterologous DNA sequences with respect to said first DNA sequence and wherein said amino acid sequence comprises an amino acid selected from the group consisting of sequence:

Met arg lys ser leu ile thr leu gly leu ala ser val ile gly thr ser ser phe leu ile pro phe thr ser lys thr ala ser ala gly thr leu asp gly lys lys gln lys ile glu ser lys gln ser glu val ala ser ser ile gly ala lys gly lys glu leu thr glu;

Met lys lys met leu val val leu leu phe ser ala leu leu leu asn gly cys gly ser gly glu ser lys ala asn thr ala gly thr pro gly val leu asp val lys leu thr gly;

Met ile arg gly ile leu ile ala val leu gly ile ala ile val gly;

Met leu lys lys val ile leu ala ala phe ile leu val gly ser;

Met ser gln gln his asp tyr val ile gly lys asn ala val ile glu thr leu lys ser asp arg leu asp leu phe pro leu leu arg leu thr lys lys pro lys val gln thr gly ile asp thr leu leu pro asp tyr lys lys gln;

gly phe glu leu ala pro gly leu phe ile leu leu phe leu phe val met ala ile gly;

Met leu lys arg thr ser phe val ser ser leu phe ile ser ser ala val leu leu ser ile leu leu pro ser gly leu ser his thr leu ser ala lys gly thr asn lys asn asn leu phe phe phe asp thr glu thr thr gly leu gly gly gly ala gly asn thr ile phe leu leu gly his ala arg val tyr glu asp arg val thr val lys gln his leu leu pro lys pro lys asn glu val ala leu tyr gln ser phe leu ser glu val asp ile thr ser leu val thr tyr asn gly lys ala phe asp tyr;

Met lys ile ser arg ile leu leu ala ala val ile leu ser ser val phe ser ile thr tyr leu gln ser asp leu gly trp phe ala lys glu gly gln met asp thr phe thr lys ala ala phe lys leu lys thr gly glu val ser asp;

Met lys gln thr val leu leu leu phe thr ala leu phe leu ser gly cys ser val ala ser ala asp asp ser val pro arg phe thr glu glu gly lys tyr ile gly ser ala asp;

Met lys lys leu val phe gly leu leu ala ile val leu phe gly cys gly leu tyr ile tyr his val trp phe gly asp;

Met leu lys lys cys ile leu leu val phe leu cys val gly leu ile gly leu ile gly cys ser lys thr asp ser pro glu asp;

Met arg lys trp ile ala ala ala gly leu ala tyr val leu tyr gly leu phe phe tyr trp tyr phe phe leu ser gly asp set ala ile pro glu ala val lys gly thr gln ala asp;

Met pro ile lys lys lys val met met cys leu ala val thr leu val phe gly ser met ser phe pro thr leu thr asn ser gly gly phe lys glu ser thr asp; and Met lys leu val pro arg phe arg lys gln trp phe ala tyr leu thr val leu cys leu ala leu ala ala ala val ser phe gly val pro ala lys ala ala glu asn pro gln thr ser val ser asn thr gly lys glu ala asp ala thr lys asn gln thr ser lys ala asp;

5. A plasmid selected from the group consisting of: pGPA14, pGPB14, and pGPP14.

6. A plasmid selected from the group consisting of: pSPB4′, pSPB5′, pSPB6′, pSPB8′, pSPB9′, pSPB11′, pSPB12′, pSPB13′, pSPB16′, pSPB19′, pSPB20′, pSPB21, pSPB23, pSPB28, pSPB29, pSPB30, pSPB31, pSPB32, pSPB34, pSPB38, pSPBA2, pSPBA8, pSPBA8 (−SPO2), pSPA9, pSPA9 (−SPO2), pSPA12, pSPA12 (−SPO2), pSPA3, pSPA26, pSPA31, pSPA42, pSPA42 (−SPO2), pSPB-A2 (−SPO2), pSPB-A2 (+SPO2), pSPB-A9 (+SPO2), pSPB-A12 (−SPO2), pSPB-A13 (−SPO2), pSPB-A13 (+SPO2), pSPB-A26 (+SPO2), pSPB-A31 (+SPO2), pSPB-A42 (+SP2), pSPA-B4, pSPA-B8′, pSPA-B9′, pSPA-B19′, pSPA-B20′, pSPA-B23, pSPA-B28, pSPA-B32, pSPA-B9′, (+sp02), pSPA-B19′ (+SPO2), pSPA-B20′ (+SPO2), and pSPA-B23 (+SP02).

* * * * *

UNITED STATES PATENT AND TRADEMARK OFFICE
CERTIFICATE OF CORRECTION

Page 1 of 3

Patent No.: 5,037,760

Dated: August 6, 1991

Inventor(s): Smith et al.

It is certified that error appears in the above-identified patent, and that said letters Patent is hereby corrected as shown.

Title page,
    item [54], line 3, after "SYNTHESIS" insert --IN--.
    item [56], "Barabara" should be --Barbara--.
    item [57], "screted" should be --secreted--.
    item [57], "sequence" should be --sequences--.
Title page, in Figure 1, "1.5 kb PstI-Hind III" should be --1.6 kb PstI-Hind III--.
In column 3, line 22, "constructions" should be --Construction--.
In column 3, line 37, " - - " should be --o-o-o--.
In column 3, line 37, "Δ-Δ" should be --▲-▲--.
In column 3, line 38, "Δ," should be --▲,--.
In column 4, line 20, "convenience," should be --convenience;--.
In column 4, lines 35-36, "com-pared secreted: should be --com-pared to secreted--.
In column 4, line 48, "both," should be --both--.
In column 5, line 31, "an" should be --and--.
In column 6, line 27, "prototrohpy" should be --prototrophy--.
In column 9, line 50, "*subtilis*Cm," should be --*subtilis* Cm,--.
In column 10, line 33, "(DSD-PAA)" should be --(SDS-PAA)--.
In column 11, lines 41-43, "Molecular Cloning, a Laboratory Manual" should be --*Molecular Cloning, a Laboratory Manual*"--.
In column 11, line 66, "Tris-HCl, pH 7.6" should be --Tris-HCl pH 7.6--.
In column 12, lines 8-9, "Tris-HCl, pH 7.2" should be --Tris-HCl pH 7.2--
In column 12, lines 48-49, "Molecular Cloning, A Laboratory Manual" should be -*Molecular Cloning, A Laboratory Manual*--.
In column 13, line 2, "described hereinbefore on pages 17 and 18" should be --described above--.
In column 14, line 21, "-182." should be -- -182).--

UNITED STATES PATENT AND TRADEMARK OFFICE
CERTIFICATE OF CORRECTION

Patent No.: 5,037,760

Dated: August 6, 1991

Inventor(s): Smith et al.

It is certified that error appears in the above-identified patent and that said Letters Patent is hereby corrected as own.

In column 14, line 46, "form" should be --from--.
In column 16, lines 27-28, "described hereinbefore on page 17" should be
--described above--.
In column 17, line 33, "described hereinbefore on page 18" should be
--described above--.
In column 17, line 51, "orogonal" should be --original--.
In column 18, lines 27-28, "described hereinbefore on page 18" should be
--described above--.
In column 18, line 29, "described herein on page 17" should be --described above--.
In column 20, line 38, "described hereinbefore on page 17" should be --described above--.
In column 21, in Table 9, in the last line of the sequence for pSPA26, after "leu" change "glu+" to --glu---.
In claim 1, column 23, line 17, "ala gly thr leu asp gly lys lys gln lys ile gly" should be --ala glu thr leu asp gly lys lys gln lys ile glu--.
In claim 1, columne 23, line 18, "gln ser gly val ala ser ser ile gly ala lys gly" should be --gln ser glu val ala ser ser ile glu ala lys glu--.
In claim 1, column 23, line 22, "gly thr pro gly val ley asp" should be --glu thr pro glu val leu asp--.
In claim 1, column 23, line 34, "asn asn lue phe" should be -asn asn leu phe--.
In claim 1, column 23, line 36, "arg val tyr gly" should be --arg val tyr glu--.
In claim 1, column 23, line 38, "asn gly val ala" should be -asn glu val ala--.
In claim 1, column 23, line 60, "ala ala gly asn" should be --ala ala glu asn--.
In claim 2, column 23, line 68, "ala gly thr leu asp gly lys" should be --ala glu thr leu asp glu lys--.

UNITED STATES PATENT AND TRADEMARK OFFICE
CERTIFICATE OF CORRECTION

Patent No.: 5,037,760

Dated: August 6, 1991

Inventor(s): Smith et al.

It is certified that error appears in the above-identified patent and that said Letters Patent is hereby corrected as shown.

In claim 2, column 24, line 3, "Mey" should be --Met--.
In claim 2, column 24, line 10, "gly thr leu" should be --glu thr leu--.
In claim 2, column 24, line 13, "gly phe glu" should be --glu phe glu--.
In claim 3, column 24, line 47, delete "to claim 2, wherein".
In claim 3, column 24, line 57, "Met ile arg glu" should be --Met ile arg gly--.
In claim 3, column 25, line 11, "val pro art" should be --val pro arg--.
In claim 3, column 25, line 16, "leu ile flu" should be --leu ile gly--.
In claim 4, column 25, line 39, "ala gly thr leu asp gly lys" should be --ala glu thr leu asp glu lys--.
In claim 4, column 25, line 40, "ile gly ala lys gly lys" should be --ile glu ala lys glu lys--.
In claim 4, column 25, line 44, "gly thr pro gly val" should be --glu thr pro glu val--.
In claim 4, column 26, line 1, "gly phe glu" should be --glu phe glu--.
In claim 4, column 26, line 13, "met asp thr phe" should be --met asp glu thr phe--.
In claim 5, column 26, line 42, "pSPA3," should be --pSPA13,--.

Signed and Sealed this

Ninth Day of November, 1993

Attest:

BRUCE LEHMAN

Attesting Officer

Commissioner of Patents and Trademarks